United States Patent [19]

Thompson et al.

[11] Patent Number: 4,952,584
[45] Date of Patent: Aug. 28, 1990

[54] 9H-PYRIDO[2,b-8]INDOLE-3-CARBOXYLIC ACID ESTER COMPOUNDS HAVING USEFUL PHARMACEUTICAL ACTIVITY

[75] Inventors: Mervyn Thompson; Ian T. Forbes, both of Harlow, England

[73] Assignee: Beecham Group p.l.c., Brentford, England

[21] Appl. No.: 307,068

[22] Filed: Feb. 6, 1989

Related U.S. Application Data

[63] Continuation-in-part of Ser. No. 1,589, Jan. 9, 1987, abandoned.

[30] Foreign Application Priority Data

Jan. 11, 1986 [GB]  United Kingdom ................. 8600651
Jan. 19, 1989 [GB]  United Kingdom ................. 8900383

[51] Int. Cl.$^5$ .................... C07D 471/04; A61K 31/44
[52] U.S. Cl. ...................................... 514/292; 546/85; 546/86; 544/126; 544/361; 514/233.2; 514/253
[58] Field of Search ...................... 514/292, 253, 233.2; 544/126, 361; 546/85, 86

[56] References Cited

FOREIGN PATENT DOCUMENTS

| | | |
|---|---|---|
| 0054507 | 6/1982 | European Pat. Off. ............. 546/87 |
| 0110814 | 6/1984 | European Pat. Off. ............. 544/126 |
| 0128415 | 12/1984 | European Pat. Off. ............. 546/87 |
| 0130140 | 1/1985 | European Pat. Off. ............. 546/87 |
| 0161575 | 11/1985 | European Pat. Off. ............. 546/87 |
| 0130141 | 1/1986 | European Pat. Off. ............. 546/87 |
| 2442513 | 3/1975 | Fed. Rep. of Germany ........ 546/87 |
| 3335323 | 4/1985 | Fed. Rep. of Germany ........ 546/87 |
| 3540653 | 5/1987 | Fed. Rep. of Germany ........ 546/87 |
| 0072751 | 5/1973 | Poland ................................ 544/126 |
| 1268773 | 3/1972 | United Kingdom ................. 546/87 |

OTHER PUBLICATIONS

Higashino et al, *Heterocycles*, vol. 15, pp. 483–487, 1981.
Kurihara et al, *Chem. Pharm. Bull.*, vol. 28, pp. 2972–2979, 1980.
Namirski et al, *Acta Pol. Pharm.*, vol. 31, pp. 137–145, 1974.
Kalinowski et al., *Current Abstracts of Chemistry*, vol. 66, Abstract 258333, 1977.
Zimmerman et al, *Archiv Der Pharmazie*, vol. 309, pp. 597–600, 1976.
Nantka et al, *Heterocyclic Compounds*, vol. 75, Abstract 76687y, p. 457, 1971.
Nantka et al., *Current Abstracts of Chemistry*, vol 49, Abstract 204 797, 1973.
Nantka et al., *Chemical Abstracts*, vol. 84, Abstract 17314n, p. 452, 1976.

*Primary Examiner*—Mary C. Lee
*Assistant Examiner*—Zinna Northington Davis
*Attorney, Agent, or Firm*—James F. Haley, Jr.; David K. Barr; Emily A. Evans

[57] ABSTRACT

A compound of formula (I) or a pharmaceutically acceptable salt thereof:

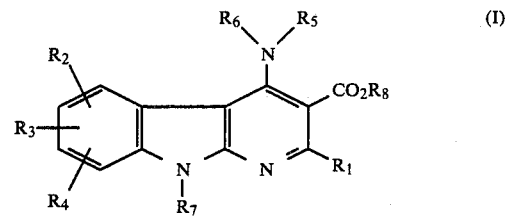

wherein: $R_1$ is hydrogen, $C_{1-6}$ alkyl, phenyl or phenyl $C_{1-4}$ alkyl wherein the phenyl moiety is optionally substituted by one or more $C_{1-6}$ alkyl, $C_{1-6}$ alkoxy, $C_{1-6}$ alkylthio, hydroxy, $C_{2-7}$ alkanoyl, halo, trifluoromethyl, nitro, amino optionally substituted by one or two $C_{1-6}$ alkyl groups or by $C_{2-7}$ alkanoyl, cyano, carbamoyl or carboxy groups; $R_2$, $R_3$ and $R_4$ are independently selected from hydrogen, $C_{1-6}$ alkyl, $C_{1-6}$ alkoxy, $C_{1-6}$ alkoxycarbonyl, $C_{1-6}$ alkylthio, hydroxy, $C_{2-7}$ alkanoyl, chloro, fluoro, trifluoromethyl, nitro, amino optionally substituted by one or two $C_{1-6}$ alkyl groups or by $C_{2-7}$ alkanoyl, cyano, carbamoyl and carboxy, and phenyl, phenyl $C_{1-4}$ alkyl or phenyl $C_{1-4}$ alkoxy in which any phenyl moiety is optionally substituted by any of these groups; $R_5$ and $R_6$ are independently selected from hydrogen, $C_{1-6}$ alkyl, $C_{3-7}$ cycloalkyl, $C_{3-7}$ cycloalkyl-$C_{1-4}$ alkyl, $C_{2-6}$ alkenyl, $C_{1-7}$ alkanoyl, $C_{1-6}$ alkylsulphonyl, di-($C_{1-6}$ alkyl)amino $C_{1-6}$ alkyl, 3-oxobutyl, 3-hydroxybutyl, phenyl, phenyl $C_{1-4}$ alkyl, benzoyl, phenyl $C_{2-7}$ alkanoyl or benzenesulphonyl any of which phenyl moieties are optionally substituted by one or two halogen, $C_{1-6}$ alkyl, $C_{1-6}$ alkoxy, $CF_3$, amino or carboxy, or $R_5$ and $R_6$ together are $C_{2-6}$ polymethylene optionally interrupted by oxygen or $NR_9$ wherein $R_9$ is hydrogen or $C_{1-6}$ alkyl optionally substituted by hydroxy; $R_7$ is hydrogen, $C_{1-6}$ alkyl, $C_{3-6}$ cycloalkyl, $C_{3-6}$ cycloalkyl-$C_{1-4}$ alkyl, $C_{2-6}$ alkenyl or $C_{2-6}$ alkynyl; and —$CO_2R_8$ is a pharmaceutically acceptable ester group, processes for its preparation and its use for the treatment or prophylaxis of anxiety or depression.

14 Claims, No Drawings

9H-PYRIDO[2,b-8]INDOLE-3-CARBOXYLIC ACID ESTER COMPOUNDS HAVING USEFUL PHARMACEUTICAL ACTIVITY

This is a continuation-in-part of Ser. No. 001,589 filed Jan. 9, 1987, now abandoned.

This invention relates to novel compounds having pharmacological activity, to a process for their preparation, to compositions containing them and to their use in the treatment of mammals.

GB 1268 773 discloses a class of compounds having antiviral activity of the general formula (A):

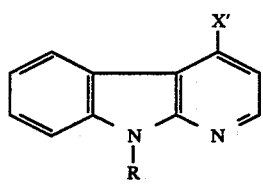

(in which R is a hydrogen atom or a substituted or unsubstituted aliphatic, araliphatic, aromatic or acyl group; X' is a halogen atom or the residue of a nucleophile, e.g. a carbon, oxygen, nitrogen or sulphur nucleophile; and in which the nucleus can be further substituted by aliphatic, araliphatic, aromatic, carboxy, carboxylic acid ester, acylamino, hydroxy, acyloxy, ether, nitro, amino, substituted amino or sulphonic acid groups or halogen atoms) and their physiologically compatible salts.

A class of compounds has been discovered, which compounds have been found to have CNS activity, in particular anxiolytic and/or anti-depressant activity.

Accordingly, the present invention provides a compound of formula (I) or a pharmaceutically acceptable salt thereof:

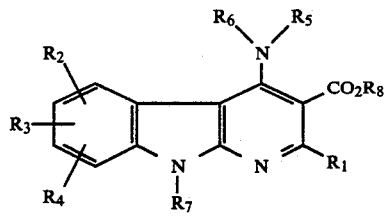

wherein:

$R_1$ is hydrogen, $C_{1-6}$ alkyl, phenyl or phenyl $C_{1-4}$ alkyl wherein the phenyl moiety is optionally substituted by one or more $C_{1-6}$ alkyl, $C_{1-6}$ alkoxy, $C_{1-6}$ alkylthio, hydroxy, $C_{2-7}$ alkanoyl, halo, trifluoromethyl, nitro, amino optionally substituted by one or two $C_{1-6}$ alkyl groups or by $C_{2-7}$ alkanoyl, cyano, carbamoyl or carboxy groups;

$R_2$, $R_3$ and $R_4$ are independently selected from hydrogen, $C_{1-6}$ alkyl, $C_{1-6}$ alkoxy, $C_{1-6}$ alkoxycarbonyl, $C_{1-6}$ alkylthio, hydroxy, $C_{2-7}$ alkanoyl, chloro, fluoro, trifluoromethyl, nitro, amino optionally substituted by one or two $C_{1-6}$ alkyl groups or by $C_{2-7}$ alkanoyl, cyano, carbamoyl and carboxy, and phenyl, phenyl $C_{1-4}$ alkyl or phenyl $C_{1-4}$ alkoxy in which any phenyl moiety is optionally substituted by $C_{1-6}$ alkyl, $C_{1-6}$ alkoxy, $C_{1-6}$ alkoxycarbonyl, $C_{1-6}$ alkylthio, hydroxy, $C_{2-7}$ alkanoyl, chloro, fluoro, trifluoromethyl, nitro, amino optionally substituted by one or two $C_{1-6}$ alkyl groups or by $C_{2-7}$ alkanoyl, cyano, carbamoyl and carboxy;

$R_5$ and $R_6$ are independently selected from hydrogen, $C_{1-6}$ alkyl, $C_{3-7}$ cycloalkyl, $C_{3-7}$ cycloalkyl-$C_{1-4}$ alkyl, $C_{2-6}$ alkenyl, $C_{1-7}$ alkanoyl, $C_{1-6}$ alkylsulphonyl, di-($C_{1-6}$ alkyl)amino $C_{1-6}$ alkyl, 3-oxobutyl, 3-hydroxybutyl, phenyl, phenyl $C_{1-4}$ alkyl, benzoyl, phenyl $C_{2-7}$ alkanoyl or benzenesulphonyl any of which phenyl moieties are optionally substituted by one or two halogen, $C_{1-6}$ alkyl, $C_{1-6}$ alkoxy, $CF_3$, amino or carboxy, or $R_5$ and $R_6$ together are $C_{2-6}$ polymethylene optionally interrupted by oxygen or $NR_9$ wherein $R_9$ is hydrogen or $C_{1-6}$ alkyl optionally substituted by hydroxy;

$R_7$ is hydrogen, $C_{1-6}$ alkyl, $C_{3-6}$ cycloalkyl, $C_{3-6}$ cycloalkyl-$C_{1-4}$ alkyl, $C_{2-6}$ alkenyl or $C_{2-6}$ alkynyl; and —$CO_2R_8$ is a pharmaceutically acceptable ester group.

Alkyl moieties within the variables $R_1$ to $R_7$ are preferably $C_{1-3}$ alkyl, such as methyl, ethyl and n- and iso-propyl.

Values for $R_1$ include hydrogen, methyl, ethyl, n- and iso- propyl, phenyl and benzyl. Preferably, $R_1$ is methyl.

Values for $R_2$, $R_3$ and $R_4$ include hydrogen, $C_{1-4}$ alkyl, $C_{1-4}$ alkoxy, hydroxy, chloro or phenyl $C_{1-4}$ alkoxy. Preferably, two of $R_2$, $R_3$ and $R_4$ represent hydrogen, and more preferably $R_2$, $R_3$ and $R_4$ each represent hydrogen.

Values for $R_5$ and $R_6$ include hydrogen, methyl, ethyl, n- and iso- propyl, n-, sec-, iso- and tert-butyl, n-, sec, iso- and neo-pentyl, cyclopentyl, cyclohexyl, cycloheptyl, cyclopentyl-$C_{1-4}$ alkyl, cyclohexyl-$C_{1-4}$ alkyl and cycloheptyl-$C_{1-4}$ alkyl, where values for $C_{1-4}$ alkyl include methylene and ethylene, but-2-enyl, but-3-enyl, 1-methylprop-2-enyl, formyl, acetyl, propionyl, methylsulphonyl, 3-dimethylaminobutyl, 3-oxobutyl, 3-hydroxybutyl, phenyl, benzyl, benzoyl, benzylcarbonyl and benzenesulphonyl, or $R_5$ and $R_6$ together form $C_4$ or $C_5$ polymethylene, —$(CH_2)_2$—O—$(CH_2)_2$— or —$(CH_2)_2$—$NR_9$—$(CH_2)_2$— where $R_9$ is preferably methyl.

Preferably $R_5$ is hydrogen and $R_6$ is hydrogen or $C_{1-6}$ alkyl.

Values for $R_7$ include hydrogen, methyl, ethyl, n- and iso-propyl, n-, iso-, sec- and tert-butyl, n-, sec-, iso- and neo-pentyl, prop-2-enyl, prop-2-ynyl, cyclopropyl, cyclobutyl, cyclopentyl and cyclopropyl-$C_{1-4}$ alkyl, cyclobutyl-$C_{1-4}$ alkyl and cyclopentyl-$C_{1-4}$ alkyl where values for $C_{1-4}$ alkyl include methylene and ethylene. Preferably $R_7$ is hydrogen, methyl or prop-2-enyl.

There is a favoured group of compounds within formula (I) of formula (II) or a pharmaceutically acceptable salt thereof:

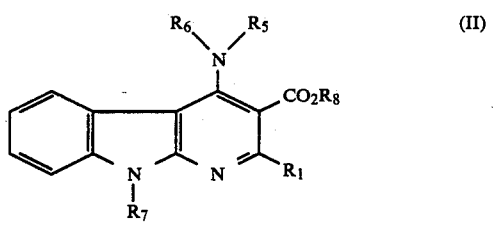

wherein $R_1$, $R_5$, $R_6$, $R_7$ and $R_8$ are as defined in formula (I).

Preferred values for $R_1$, $R_5$, $R_6$ and $R_7$ are as described under formula (I).

There is a preferred group of compounds within formula (II) of formula (III) or a pharmaceutically acceptable salt thereof:

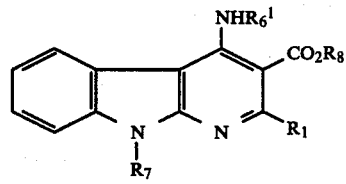

wherein $R_6^1$ is hydrogen or $C_{1-6}$ alkyl and $R_1$, $R_7$ and $R_8$ are as defined in formula (I).

Preferred values for $R_1$, $R_7$ and $R_6^1$ are as described for the corresponding variables in formula (I).

The compounds of the formula (I) can form acid addition salts with acids, such as the conventional pharmaceutically acceptable acids, for example, maleic, hydrochloric, hydrobromic, phosphoric, acetic, fumaric, salicylic, citric, lactic, mandelic, tartaric and methanesulphonic.

Suitable examples of pharmaceutical esters of the compounds of formula (I) include $C_{1-6}$ alkyl esters, such as methyl, ethyl, n- and iso-propyl, n-, sec- and tert-butyl esters, $C_{2-6}$ alkenyl esters such as vinyl, prop-1-enyl, prop-2-enyl, 1-methylvinyl, but-1-enyl, but-3-enyl, 1-methylenepropyl and 1-methylprop-2-enyl, (in both their E and Z forms where stereoisomerism exists), $C_{2-6}$ alkynyl esters such as prop-2-ynyl, $C_{3-6}$ cycloalkyl esters and $C_{3-6}$ cycloalkyl-$C_{1-4}$ alkyl esters such as cyclopropylmethyl. Preferably the pharmaceutically acceptable ester is the methyl, ethyl, propyl, prop-2-enyl or prop-2-ynyl ester, i.e. $R_8$ is methyl, ethyl, propyl, prop-2-enyl or prop-2-ynyl.

It will be appreciated that the compounds of formula (I) in which $R_5$, $R_6$ or $R_7$ is hydrogen may exist tautomerically in more than one form. The invention extends to each of these forms and to mixtures thereof.

Compounds of formula (I) may also form solvates such as hydrates, and the invention also extends to these forms. When referred to herein, it is understood that the term "compound of formula (I)" also includes solvates thereof.

The present invention also provides a process for the preparation of a compound of formula (I), or a pharmaceutically acceptable salt thereof, which process comprises the reaction of a compound of formula (IV):

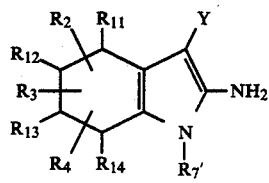

with a compound of formula (V):

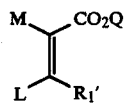

wherein $R_1'$ is $R_1$ as defined in formula (I) or a group convertible thereto, $R_2$, $R_3$ and $R_4$ are as defined in formula (I), $R_7'$ is $R_7$ as defined in formula (I) or an N-protecting group, $R_{11}$, $R_{12}$, $R_{13}$ and $R_{14}$ are each hydrogen or $R_{11}$ and $R_{12}$, and $R_{13}$ and $R_{14}$ together represent a bond, Q is a protecting group, L is a leaving group and M is hydrogen or L and M together represent a bond, and Y is a group CN or $COL_1$, where $L_1$ is a leaving group; and thereafter, optionally or as necessary, when Y is a group $COL_1$, converting the resulting hydroxy group to a leaving group and reacting the latter with a compound $HNR_5R_6$, removing any $R_7'$ N-protecting group, converting $R_1'$ when other than $R_1$ to $R_1$, converting $R_{11}$, $R_{12}$, $R_{13}$ and $R_{14}$ when hydrogen to two bonds, interconverting $R_2$, $R_3$, $R_4$, $R_5$, $R_6$, or $R_7$, removing Q, forming a pharmaceutically acceptable ester of the resultant acid and/or forming a pharmaceutically acceptable salt of the compound of formula (I).

Suitable examples of the leaving group L include halogens, such as chloro and bromo, hydroxy, $C_{1-6}$ acyloxy such as acetoxy or $C_{1-6}$ alkoxy, such as methoxy or ethoxy, preferably methoxy. When L is hydroxy, it will be appreciated that the compound of formula (V) exists in more than one tautomeric form.

The reaction of compounds of formulae (IV) and (V) comprises a condensation step followed by a cyclisation step, the acyclic enamine ester intermediate optionally being isolated before cyclisation.

The condensation step may be carried out under conditions conventional for condensation reactions, at elevated temperatures in an inert solvent such as toluene, benzene, ethanol, pyridine, dimethylformamide or dioxan in the presence of a catalyst such as para-toluene-sulphonic acid, with water separation.

The cyclisation of the enamine ester may also be carried out under conventional conditions, in the presence of a strong base such as an alkali metal alkoxide, for example sodium methoxide in a suitable solvent such as methanol in toluene, at elevated temperature, or in the presence of a Lewis acid such as $ZnCl_2$, $SnCl_4$ or $CuOCOCH_3$ in n-butyl acetate at elevated temperature.

Suitable examples of protecting groups Q include the groups hereinbefore described for $R_8$, and benzyl wherein the benzyl moiety is optionally substituted in the phenyl ring by one or two of halogen, $CF_3$, $C_{1-6}$ alkoxy, $C_{1-6}$ alkyl or nitro. The protecting groups Q may be removed by conventional hydrolysis or hydrogenolysis to yield the free acid which can then be esterified under conventional conditions by reaction with the appropriate alcohol $R_8OH$, optionally with prior conversion of the acid to the acid chloride by reaction with a suitable chlorinating agent such as thionyl chloride, or with an alkylating agent $R_8X$ where X is a leaving group such as chloro or bromo.

Alternatively the conversion of Q to hydrogen can proceed by way of an amide. Suitable examples include the unsubstituted amide and those wherein the amide moiety is substituted by one or two groups selected from $C_{1-6}$ alkyl and phenyl or phenyl $C_{1-4}$ alkyl optionally substituted as described above for optional substituents in the phenyl ring of a benzyl ester, or disubstituted by $C_{3-5}$ polymethylene optionally interrupted by oxygen or $NR_{10}$ wherein $R_{10}$ is hydrogen or $C_{1-6}$ alkyl e.g. morpholino or piperazino.

The intermediate amide may be hydrolysed to the free acid which can then be esterified as described above.

Conversion of $R_{11}$, $R_{12}$, $R_{13}$ and $R_{14}$ when hydrogen to two bonds may be carried out under conventional aromatisation conditions, with an oxidising agent such as 2,3-dichloro-5,6-dicyano-1,4-benzoquinone, in an inert solvent such as benzene or toluene.

Alternatively, the conversion may be carried out by catalytic dehydrogenation using a conventional metal catalyst such as Pd/C in a suitable solvent such as xylene or mesitylene at elevated temperature, for example 100°–180° C., or by sulphur dehydrogenation under conventional conditions.

In the compound of formula (IV), it is preferred that $R_{11}$ and $R_{12}$, and $R_{13}$ and $R_{14}$ together represent a bond.

Suitable examples of $R_7'$ N-protecting groups include benzyl, mono- or di-methoxybenzyl, which may be removed conventionally, for example by heating with AlCl$_3$ in benzene, or by treatment with trifluoroacetic acid and anisole, optionally in the presence of sulphuric acid and optionally with heating.

Conversion of $R_7$ hydrogen to $R_7$ alkyl, alkenyl or alkynyl may be carried out by treatment of the NH compound with a strong base, such as sodium hydride in dimethyl formamide, followed by reaction with the appropriate alkyl, alkenyl or alkynyl halide, preferably the iodide or bromide.

Suitable examples of a leaving group $L_1$ when Y is COL$_1$, include hydroxy and alkoxy such as ethoxy or methoxy, more preferably methoxy. The reaction of the compounds of formulae (IV) and (V) gives a resulting compound having a hydroxy group in the 4-position of the pyridine ring. The hydroxy group may be converted to a leaving group such as those defined above for L, preferably halo such as chloro, by reaction with a halogenating agent such as phosphorus oxychloride or phosphorus oxybromide. The leaving group may be displaced by the compound HNR$_5$R$_6$ under conventional conditions for nucleophilic aromatic displacements, at elevated temperatures in an inert solvent such as toluene, methanol, ethanol, pyridine, dimethyl formamide or dioxan. Alternatively, the reaction may be carried out in neat HNR$_5$R$_6$ which functions as the solvent.

Conversion of $R_5$ and $R_6$ hydrogen to other $R_5/R_6$ may be carried out in accordance with conventional procedures for the alkylation or acylation of a primary amine. Acylation may be carried out by reaction with the appropriate acyl halide. However, $R_5/R_6$ other than hydrogen or acyl groups are preferably introduced via the route in which Y is COL$_1$ in the compound of formula (IV), by displacement of the leaving group with the compound HNR$_5$R$_6$ as discussed above.

Interconversion of $R_2$, $R_3$ and $R_4$ may be carried out by conventional procedures for the conversion of aromatic substituents. Thus, for example, a chloro substituent in the 6 position may be introduced by direct chlorination using standard conditions, such as chlorine in chloroform.

Preferably $R_2$, $R_3$ and $R_4$ are all hydrogen in the compound of formula (IV) and the introduction of the desired substituents $R_2$, $R_3$ and $R_4$ is carried out after the reaction between the compounds of formulae (IV) and (V), to avoid the production of unwanted side products during the preparation of the compound of formula (IV).

For the preparation of compounds of formula (I) in which $R_1$ is hydrogen, the compound of formula (V) may be used in which L and M together represent a bond and $R_1'$ is a C$_{1-6}$ alkoxycarbonyl group. The reaction with the compound of formula (IV) may then be followed by a decarboxylation step to give $R_1$ hydrogen. Alternatively, a compound of formula (V) may be used in which L is a leaving group and $R_1'$ is hydroxy. In the resulting compound, the $R_1'$ hydroxy may be converted to hydrogen by first replacing it by chloro by conventional chlorination with a chlorinating agent such as phosphorus oxychloride followed by reductive dehalogenation under conventional conditions, for example zinc in acetic acid.

Pharmaceutically acceptable salts may be prepared conventionally by reaction with the appropriate acid or derivative.

A class of intermediates comprises compounds of formula (VI) or salts, esters or amides thereof:

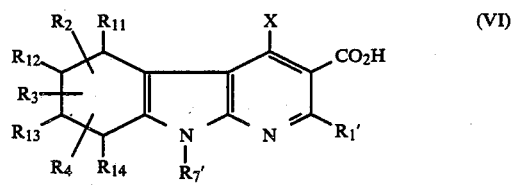

wherein $R_1'$ is as defined in formula (V), X is NH$_2$, OH or chloro and $R_7'$, $R_2$, $R_3$, $R_4$, $R_{11}$, $R_{12}$, $R_{13}$ and $R_{14}$ are as defined in formula (IV), provided that when X is NH$_2$, $R_{11}$ and $R_{12}$, and $R_{13}$ and $R_{14}$ represent two bonds, $R_1'$ is $R_1$ and $R_7'$ is $R_7$, the compound is the acid, an amide or an ester other than of an alcohol $R_8$OH. Compounds of formula (VI) in which X is NH$_2$, $R_2$, $R_3$, $R_4$, $R_{11}$, $R_{12}$, $R_{13}$ and $R_{14}$ are all hydrogen, $R_1'$ is methyl and $R_7'$ is benzyl or cyclohexyl, in the form of the ethyl ester, have all been described by H. J. Roth et al., Arch. Pharmaz., 1976, 309, 597. Novel compounds of formula (VI) also form part of the invention.

Compounds of formulae (IV) and (V) are known or can be prepared by analogous processes to those used for preparing known compounds. Thus, for example, the compounds of formula (IV) where $R_{11}$, $R_{12}$, $R_{13}$ and $R_{14}$ are each hydrogen may be prepared by the reaction of a compound of formula (VII):

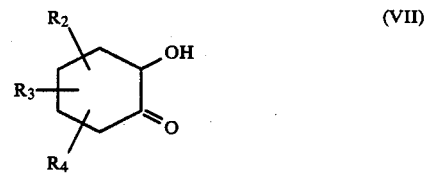

with CH$_2$(CN)$_2$ and an alkylamine such as 4-methoxybenzylamine or benzylamine by a procedure analogous to that described by H. J. Roth et al., Arch. Pharmaz., 1975, 308, 179.

Alternatively, the compound of formula (VII) may be reacted with NCCH$_2$CO$_2$C(CH$_3$)$_3$ and an alkylamine such as benzylamine by a procedure analogous to that described by H. J. Roth et al., Arch. Pharmaz., 1975, 308, 179. This gives a compound of formula (IV) in which $L_1$ is t-butoxy, which may be converted to other $L_1$ by conventional procedures.

Compounds of formula (IV) where $R_{11}$ and $R_{12}$, and $R_{13}$ and $R_{14}$ together represent a bond may be prepared by procedures conventional in indole chemistry.

Thus, for example, a compound of formula (VIII):

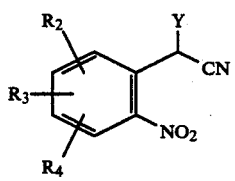

(VIII)

wherein $R_2$, $R_3$ and $R_4$ are as defined in formula (I) and Y is as defined in formula (IV), may be reduced and cyclised by treatment with a metal such as zinc, iron or tin in an acid such as acetic acid, in an inert solvent such as toluene at elevated temperature by a procedure analogous to that described by K. L. Munshi et al J.Het.-Chem. 1977, 14, 1145. Alternatively, when Y is CN the reduction and cyclisation may be effected by treatment with aqueous sodium dithionite. These procedures give a compound of formula (IV) in which $R_7'$ is hydrogen and which may be N-substituted under conventional conditions as described above to give other compounds of formula (IV).

Compounds of formula (VIII) are known or may be prepared by procedures analogous to those for preparing known compounds.

The present invention also provides a pharmaceutical composition, which comprises a compound of formula (I) or a pharmaceutically acceptable salt thereof, and a pharmaceutically acceptable carrier.

A pharmaceutical composition of the invention, which may be prepared by a mixture, is usually adapted for oral or parenteral administration and, as such, may be in the form of tablets, capsules, oral liquid preparations, powders, granules, lozenges, reconstitutable powders, or injectable or infusable solutions or suspensions. Orally administrable compositions are generally preferred.

Tablets and capsules for oral administration may be in unit dose form, and may contain conventional excipients, such as binding agents, fillers, tabletting lubricants, disintegrants and acceptable wetting agents. The tablets may be coated according to methods well known in normal pharmaceutical practice.

Oral liquid preparations may be in the form of, for example, aqueous or oily suspensions, solutions, emulsions, syrups or elixirs, or may be in the form of a dry product for reconstitution with water or other suitable vehicle before use. Such liquid preparations may contain conventional additives such as suspending agents, emulsifying agents, non-aqueous vehicles (which may include edible oils), preservatives, and, if desired, conventional flavourings or colourants.

For parenteral administration, fluid unit dosage forms are prepared utilising a compound of the invention or pharmaceutically acceptable salt thereof and a sterile vehicle. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum.

Parenteral suspensions are prepared in substantially the same manner, except that the compound is suspended in the vehicle instead of being dissolved, and sterilization cannot be accomplished by filtration. The compound can be sterilised by exposure to ethylene oxide before suspension in a sterile vehicle. Advantageously, a surfactant or wetting agent is included in the composition to facilitate uniform distribution of the compound.

The composition may contain from 0.1% to 99% by weight, preferably from 10 to 60% by weight, of the active material, depending on the method of administration.

The invention also provides a compound of formula (I) or a pharmaceutically acceptable salt thereof, for pharmaceutical use. By pharmaceutical use is meant the treatment or prophylaxis of disorders in mammals including humans. Compounds of formula (I) and their pharmaceutically acceptable salts are of particular use in the treatment of CNS disorders, in particular anxiety or depression.

The invention further provides a method of treatment of CNS disorders, in particular anxiety or depression in mammals including humans, which comprises administering to the sufferer an anti-depressant or anxiolytic effective amount of a compound of formula (I) or a pharmaceutically acceptable salt thereof.

The dose of the compound used in the treatment of CNS disorders, such as anxiety or depression will vary in the usual way with the seriousness of the disorders, the weight of the sufferer, and other similar factors. However, as a general guide suitable unit doses may be 0.05 to 1000 mg, more suitably 0.05 to 10.0 mg, for example 0.2 to 1 mg; and such unit doses may be administered more than once a day, for example two or three times a day, so that the total daily dosage is in the range of about 0.01 to 100 mg/kg; and such therapy may extend for a number of weeks or months.

Within the above indicated dosage range, no adverse toxicological effects are indicated with the compounds of the invention.

The following Examples illustrate the preparation of the compounds of the invention. The following Descriptions illustrate the preparation of intermediates to the compounds of the present invention.

In the following Descriptions and Examples, all temperatures recited are in degrees Centigrade.

DESCRIPTION 1

2-Amino-1-benzyl-3-cyano-4,5,6,7-tetrahydroindole (D1)

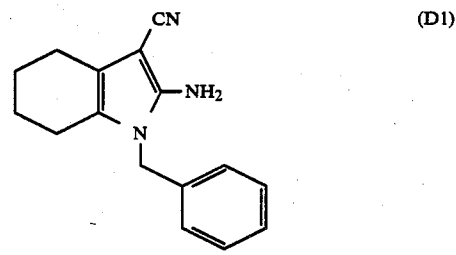

The title compound was prepared in 65% yield using a procedure similar to that described by H. J. Roth et al., Arch. Pharmaz., 1975, 308, 179. Product was obtained as pink crystals, m.p. 128°–130°.

NMR (CDCl$_3$)δ: 1.60–1.90 (4H, m), 2.25–2.60 (4H, m), 3.62 (2H, s, ex D$_2$O), 4.90 (2H, s), 6.97–7.47 (5H, m).

Found: C, 76.48; H, 6.72; N, 16.55. C$_{16}$H$_{17}$N$_3$ requires C, 76.46; H, 6.82; N, 16.72%

DESCRIPTION 2

4-Amino-9-benzyl-2-methyl-5,6,7,8-tetrahydro-9H-pyrido[2,3-b]indole-3-carboxylic acid, ethyl ester (D2)

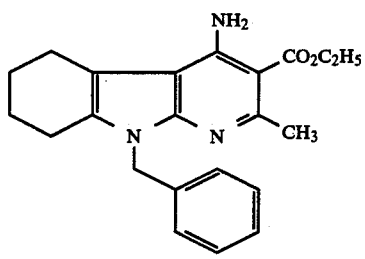

(D2)

The title compound was prepared using a modified procedure (see below) to that described by H. J. Roth et al., Arch. Pharmaz., 1976, 309, 597. 2-Amino-1-benzyl-3-cyano-4,5,6,7-tetrahydroindole (D1) (1.255 g; 5 mM) was added to a solution of ethyl acetoacetate (0.655 g; 5 mM) in toluene (60 ml) containing para-toluenesulphonic acid (30 mg), and the mixture refluxed vigorously for 1 h with water separation (Dean and Stark apparatus). To the cooled solution was then added 1M sodium ethoxide in ethanol (6 ml) and the mixture refluxed for a further 2 h. The cooled solution was poured onto water, and the pH of the stirred mixture adjusted to 7 using 5M hydrochloric acid. The toluene layer was then separated, and the aqueous phase re-extracted with toluene. The combined organic phase was washed with brine, dried and evaporated to give a brown oil (1.5 g). Crystallisation from ethanol afforded the title compound as off-white needles (0.8 g; 44%), m.p. 145.5°–147°.

NMR (CDCl$_3$)δ: 1.43 (3H, t, J=8), 1.60–1.90 (4H, m), 2.30–2.60 (2H, m), 2.75 (3H, s), 2.80–3.00 (2H, m), 4.25–4.52 (2H, q, J=8), 5.38 (2H, s), 6.20–6.45 (2H, s ex D$_2$O), 7.05–7.35 (5H, m).

Found: C, 72.59; H, 6.97; N, 11.55. C$_{22}$H$_{25}$N$_3$O$_2$ requires C, 72.70; H, 6.93; N, 11.56%.

DESCRIPTION 3

4-Amino-2-methyl-9-phenylmethyl-9H-pyrido[2,3-b]indole-3-carboxylic acid, ethyl ester (D3)

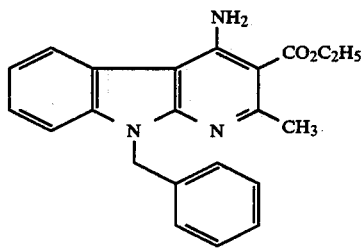

(D3)

A solution of the tetrahydro intermediate (D2) (0.91 g; 2.5 mM) in benzene (20 ml) was added dropwise to 2,3-dichloro-5,6-dicyano-1,4-benzoquinone (1.15 g; 5 mM) dissolved in benzene (20 ml), with vigorous stirring. The mixture was then refluxed for approximately 15 minutes. The cooled solution was filtered and evaporated to dryness. Chromatography of the residue on silica gel (30 g) with dichloromethane elution afforded a white solid (0.69 g; 76%) which was crystallised from ethanol to yield the title compound as white needles (0.4 g; 45%), m.p. 139°–140°.

NMR (CDCl$_3$)δ: 1.42 (3H, t, J=7), 2.84 (3H, s), 4.40 (2H, q, J=7), 5.63 (2H, s), 6.70 (2H, s, ex D$_2$O), 7.20–7.35 (8H, m), 7.75–7.90 (1H, m).

Observed M+ 359.1636.
C$_{22}$H$_{21}$N$_3$O$_2$ requires 359.1634.
Found: C, 73.73; H, 6.02; N, 11.50. C$_{22}$H$_{21}$N$_3$O$_2$ requires C, 73.52; H, 5.89; N, 11.69%.

DESCRIPTION 4

4-Amino-2-methyl-9H-pyrido[2,3-b]indole-3-carboxylic acid, hydrochloride (D4)

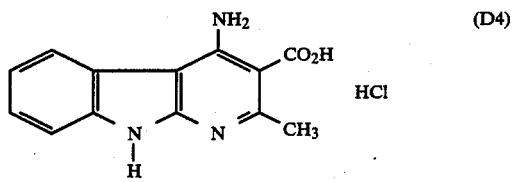

(D4)

A solution of the N-benzyl intermediate (D3) (5 g; 13.9 mM) in dry benzene (174 ml) was added dropwise over 0.5 h to aluminium chloride (10.44 g; 78.5 mM) suspended in benzene (90 ml), with vigorous stirring. The mixture was then heated in an oil bath at 65° for 1.5 h. After cooling, the solvent was decanted off and the residue washed twice with benzene. The brown residue was then digested with water (253 ml) and 5M hydrochloric acid (7 ml). The resultant pink solid was filtered, washed with water (×3) and dried at 60° in vacuo to afford the title compound (3.9 g; 100%), m.p. 230°–232° (decomposition).

NMR (DMSO)δ: 2.85 (3H, s), 7.25 (1H, s, ex D$_2$O), 7.27–7.83 (3H, m), 8.39 (2H, s, ex D$_2$O), 8.42–8.60 (1H, m), 12.65 (1H, s, ex D$_2$O).

Observed M+ 241.0840.
C$_{13}$H$_{11}$N$_3$O$_2$ requires 241.0851.

DESCRIPTION 5

2-Amino-3-cyano-1-(4-methoxyphenyl)methyl-4,5,6,7-tetrahydroindole (D5)

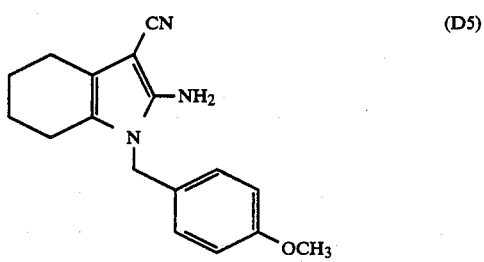

(D5)

The title compound was prepared in 64% yield using a procedure similar to that described by H. J. Roth et al., Arch. Pharmaz., 1975, 308, 179. Product crystallised as yellow needles from methanol.

m.p. 122°–126°.

NMR (CDCl$_3$)δ: 1.70–1.85 (4H,m), 2.32–2.40 (2H,m), 2.43–2.51 (2H,m), 3.62 (2H, broad s), 3.80 (3H,s), 4.80 (2H,s), 6.87 (2H,d,J=9), 6.96 (2H,d,J=9).

Observed M+ 281.1529.
C$_{17}$H$_{19}$N$_3$O requires: 281.1528.
Found: C, 72.42; H, 6.91; N, 14.94. C$_{17}$H$_{19}$N$_3$O requires: C, 72.57; H, 6.81; N, 14.93%.

DESCRIPTION 6

4-Amino-9-(4-methoxyphenyl)methyl-2-methyl-5,6,7,8-tetrahydro-9H-pyrido[2,3-b]indole-3-carboxylic acid, methyl ester (D6)

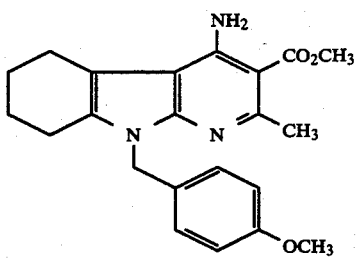

A solution of the aminonitrile (D5) (34.40 g; 0.12M), methyl β-methoxycrotonate (17.93 g; 0.138M) and para-toluenesulphonic acid (1.3 g; 6.8 mM) in toluene (520 ml) was vigorously refluxed with distillation for 1 h, during which time 50 ml distillate was collected. The brown solution was cooled, and 1M sodium methoxide in methanol (144 ml; 144 mM) was added. The solution was then refluxed for a further 3 h, with the removal of 200 ml distillate. The solution was cooled and poured onto saturated brine (260 ml). With vigorous stirring, the pH was adjusted to 8 using 5M hydrochloric acid (27 ml). Care was taken to avoid the pH being <7 at any stage. The toluene layer was separated, and the aqueous layer extracted with toluene (×2). The combined toluene extracts were washed with brine, dried and evaporated to dryness to afford a dark oil. Crystallisation from methanol afforded the title compound as a buff powder (28.5 g; 61%). Recrystallisation from methanol afforded analytical material.

m.p. 130°–131°.

NMR (CDCl$_3$)δ: 2.8 (4H,m), 2.4–2.5 (2H,m), 2.71 (3H,s), 2.85–2.90 (2H,m), 3.75 (3H,s), 3.88 (3H,s), 5.27 (2H,s), 6.33 (2H, broad s), 6.77 (2H,d,J=10), 7.04 (2H,d,J=10).

Observed M+ 379.1885.

C$_{22}$H$_{25}$N$_3$O$_3$ requires: 379.1896.

Found: C, 69.54; H, 6.63; N, 11.06. C$_{22}$H$_{25}$N$_3$O$_3$ requires: C, 69.64; H, 6.64; N, 11.07%.

DESCRIPTION 7

4-Amino-9-(4-methoxyphenyl)methyl-2-methyl-9H-pyrido[2,3-b]indole-3-carboxylic acid, methyl ester (D7)

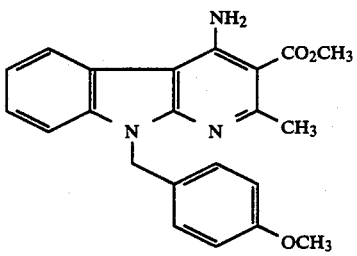

A solution of the tetrahydro intermediate (D6) (21.35 g; 56 mM) in toluene (190 ml) was added dropwise to a vigorously stirred solution of 2,3-dichloro-5,6-dicyano-1,4-benzoquinone (25.6 g; 113 mM) in toluene (190 ml). The resultant solution was transferred to a pre-heated oil bath at 120°, and this temperature maintained for 30 minutes at which time a buff coloured precipitate had formed. The reaction mixture was then filtered hot, and the solids washed with toluene. The toluene solution was then evaporated to dryness. The above solids were extracted twice with hot dichloromethane, which was then evaporated to dryness. The combined material from the toluene and dichloromethane solutions was chromatographed on silica (200 g) with dichloromethane elution. The appropriate fractions were combined and evaporated to dryness to afford the title compound (14.24 g; 67%) as an off-white solid.

m.p. 142°–145°.

NMR (CDCl$_3$)δ: 2.83 (3H,s), 3.73 (3H,s), 3.95 (3H,s), 5.57 (2H,s), 6.72 (2H, broad s), 6.77 (2H,m), 7.15–7.35 (5H,m), 7.80–7.85 (1H,m).

Observed M+ 375.1578.

C$_{22}$H$_{21}$N$_3$O$_3$ requires: 375.1582.

Found: C, 70.35; H, 5.67; N, 11.32. C$_{22}$H$_{21}$N$_3$O$_3$ requires: C, 70.38; H, 5.64; N, 11.19%.

DESCRIPTION 8

4-Amino-9-(4-methoxyphenyl)methyl-2-methyl-5,6,7,8-tetrahydro-9H-pyrido[2,3-b]indole-3-carboxylic acid, ethyl ester (D8)

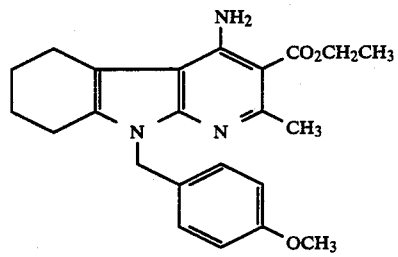

The title compound was prepared in 64% yield from 2-amino-3-cyano-1-(4-methoxyphenyl)methyl-4,5,6,7-tetrahydroindole (D5) and ethyl β-ethoxycrotonate in a procedure similar to Description 6. Product was obtained as beige crystals from ethanol.

m.p. 108°–10° C.

NMR (CDCl$_3$)δ: 1.37 (3H,t,J=8), 1.60–1.90 (4H,m), 2.25–2.55 (2H,m), 2.66 (3H,s), 2.65–2.95 (2H,m), 3.65 (3H,s), 4.27 (2H,q,J=8), 5.17 (2H,s), 6.19 (2H, broad s, ex D$_2$O), 6.62 (2H,d,J=9), 6.93 (2H,d,J=9).

DESCRIPTION 8 (Alternative Procedure)

4-Amino-9-(4-methoxyphenyl)methyl-2-methyl-5,6,7,8-tetrahydro-9H-pyrido[2,3-b]indole-3-carboxylic acid, ethyl ester (D8)

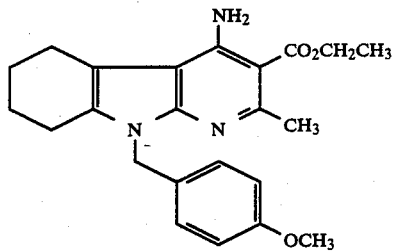

A solution of 2-amino-1-(4-methoxyphenyl)methyl-4,5,6,7-tetrahydro-1H-indole-3-carbonitrile (EP 0249301A) (2.00 g, 7.1 mM), ethyl β-ethoxycrotonate (1.30 g, 8.2 mM) and para toluenesulphonic acid (0.08 g; 0.4 mM) in toluene (25 ml) was vigorously refluxed with distillation until no more water distilled over. The solution was cooled and n-butyl acetate (25 ml) and tin (IV) chloride (1.7 ml; 14.5 mM) were added. The solution was then refluxed for 10 minutes and allowed to cool. The reaction mixture was poured onto 1% aqueous sodium hydroxide solution (50 ml) and shaken with dichloromethane (20 ml). The organic layer was separated, and the aqueous layer further extracted with dichloromethane (×2). The combined organic phase was washed with water and brine, dried (Na$_2$SO$_4$) and evaporated to dryness to afford a crude solid. Crystallisation from ethanol gave the title compound (D8) (1.4 g, 50%) as a pale yellow solid m.p. 112°-3°.

DESCRIPTION 9

4-Amino-9-(4-methoxyphenyl)methyl-2-methyl-9H-pyrido[2,3-b]indole-3-carboxylic acid, ethyl ester (D9)

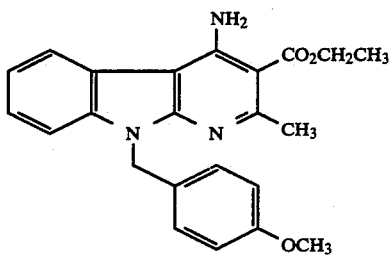
(D9)

The title compound was prepared in 73% yield from 4-amino-9-(4-methoxyphenyl)methyl-2-methyl-5,6,7,8-tetrahydro-9H-pyrido[2,3-b]indole-3-carboxylic acid, ethyl ester (D8) and 2,3-dichloro-5,6-dicyano-1,4-benzoquinone in a procedure similar to Description 7, using benzene as solvent instead of toluene. Product was obtained as white crystals from ethanol.
m.p. 138°-40° C.
NMR (CDCl$_3$)δ 1.45 (3H,t,J=8), 2.88 (3H,s), 3.75 (3H,s), 4.45 (2H,q,J=8), 5.60 (2H,s), 6.60–6.88 (2H,m), 6.70 (2H,broad s, ex D$_2$O), 7.10–7.45 (5H,m), 7.85 (1H,m).
Observed M$^+$ 389.1738.
C$_{23}$H$_{23}$N$_3$O$_3$ requires: 389.1739.
Found: C, 71.18; H, 6.00; N, 10,80. C$_{23}$H$_{23}$N$_3$O$_3$ requires: C, 70.93; H, 5.95; N, 10.79%.

DESCRIPTION 10

4-Amino-9-(4-methoxyphenyl)methyl-2-methyl-9H-pyrido[2,3-b]indole-3-carboxylic acid (D10)

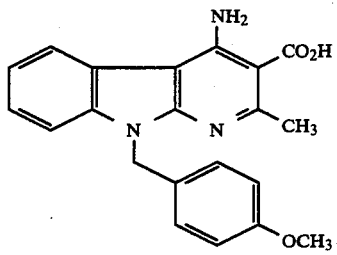
(D10)

A solution of the methyl ester (D7) (6 g; 16 mM) in 10% aqueous sodium hydroxide (42 ml) and ethanol (42 ml) was refluxed for 2 h.

The solution was allowed to cool, diluted with an equivalent volume of water and brought to pH 5 with 5M hydrochloric acid. The resulting suspension was filtered off, washed with water and dried in vacuo to yield the title compound as a white solid (5.33 g, 96%), m.p. 206°-208°.
NMR (d$_6$ DMSO)δ 2.75 (3H, s), 3.7 (3H, s), 5.55 (2H, broad s), 6.85 (2H, d, J=8), 7.1–7.6 (7H, m), 8.2–8.4 (1H, m).

DESCRIPTION 11

4-Amino-2,9-dimethyl-9H-pyrido[2,3-b]indole-3-carboxylic acid (D11)

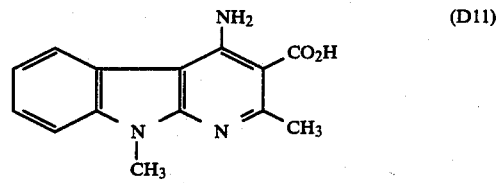
(D11)

The title compound was prepared from the ester (E2) using a procedure similar to that described in Description 10.
m.p. 230°-232°.
NMR (d$_6$-DMSO)δ 2.67 (3H, s), 3.8 (3H, s), 7.05–7.6 (5H, m), 8.15–8.35 (1H, broad d, J=7).
Observed M$^+$ 255.1026.
C$_{14}$H$_{13}$N$_3$O$_2$ requires 255.1008.

DESCRIPTION 12

4-Amino-9-(4-methoxyphenyl)methyl-2-phenyl-5,6,7,8-tetrahydro-9H-pyrido[2,3-b]indole-3-carboxylic acid, methyl ester (D12)

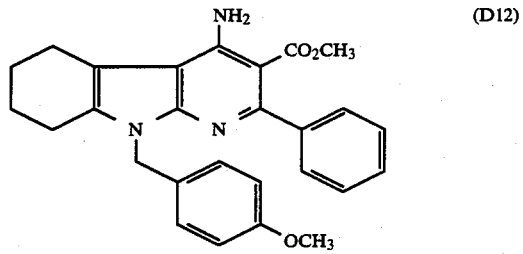
(D12)

Using a procedure similar to Description 6, the title compound (D12) was prepared in 73% yield from 2-amino-3-cyano-1-(4-methoxyphenyl)methyl-4,5,6,7-tetrahydroindole (D5) and methyl-3-methoxycinnamate.
m.p. 192°-4° (from dichloromethane-methanol)
Found: C, 73.10; H, 6.31; N, 9.57. C$_{27}$H$_{27}$N$_3$O$_3$ requires C, 73.45; H, 6.16 and N, 9.52%.

DESCRIPTION 13

4-Amino-9-(4-methoxyphenyl)methyl-2-methyl-9H-pyrido[2,3-b]indole-3-carboxylic acid, 2-propenyl ester (D13)

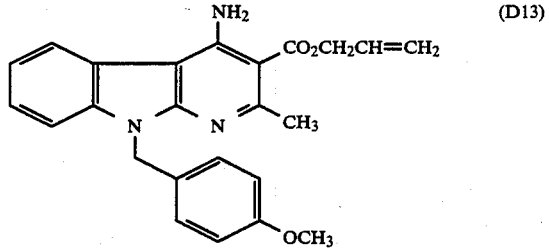
(D13)

To a solution of the carboxylic acid (D10) (1.85 g; 5 mM) in dry dimethylformamide (35 ml) was added potassium carbonate (1.54 g) followed by allylbromide (0.66 g), under a nitrogen atmosphere. This mixture was stirred at room temperature for 16 h, then poured onto water (220 ml) and extracted with ethyl acetate. The organic layer was washed with brine, dried and evaporated to give a white solid (1.97 g; 95%).

NMR (CDCl$_3$)δ 2.55 (3H, s), 3.40 (3H, s), 4.55 (2H, d, J=6), 5.00 (1H, dd, J=10, 2), 5.12 (1H, dd, J=16,2), 5.25 (2H, s), 5.7–5.85 (1H, m), 6.35–6.50 (4H, m), 6.8–7.05 (5H, m), 7.5 (1H, d, J=8).

DESCRIPTION 14

2-Nitrophenylcyanoacetic acid, methyl ester (D14)

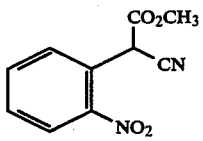

The title compound was prepared in 97% yield using a modified procedure (see below) to that described by C. A. Grob et al., Helv. Chim. Acta, 1961, 44, 1748.

A solution of methyl cyanoacetate (24.75 g; 0.25M) in dimethylformamide (70 ml) was added dropwise over 40 minutes to a stirred suspension of sodium hydride (8.25 g; 0.275M) in dimethylformamide (250 ml) at 0° under nitrogen atmosphere. The solution was stirred for 0.5 h, then a solution of 2-fluoronitrobenzene (17.65 g; 0.125M) in dimethylformamide (70 ml) added. After stirring for 16 h at room temperature, the red solution was poured onto excess brine, and extracted with ether (×6). The aqueous layer was then acidified with hydrochloric acid (5M) until the red colour was discharged. The resultant solution was extracted with ether (×4) and the combined organic extracts washed with brine, dried and evaporated to afford the title compound as a yellow oil (26.7 g; 97%) which slowly solidified.

NMR (CDCl$_3$)δ: 3.87 (3H,s), 5.70 (1H,s), 7.50–7.85 (3H, m), 8.15–8.35 (1H,m).

DESCRIPTION 15

2-Aminoindole-3-carboxylic acid, methyl ester (D15)

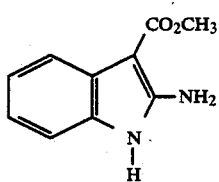

The title compound was prepared in 84% yield using a modified procedure (see below) to that described by K. L. Munshi et al., J. Het. Chem., 1977, 14, 1145.

A solution of the nitro compound (D14) (20 g; 90.9 mM) in toluene (150 ml) and acetic acid (50 ml) was heated to 80° (internal temperature). Zinc powder (42 g; 0.64M) was added slowly, portionwise, over 35 minutes with vigorous stirring keeping temperature between 80°–90°. External heating was removed after initial exotherm was observed. When addition of zinc was complete, heating was recommenced, keeping temperature at 80°, for 30 minutes. The solution was cooled and filtered, then evaporated to dryness. The residue was dissolved in ethyl acetate, washed with aqueous sodium bicarbonate, brine then dried and evaporated to give the title compound (14.5 g; 84%) as a brown solid, which was used directly in Description 16.

NMR (CDCl$_3$)δ: 3.8 (3H,s), 6.1 (2H, broad s), 6.8–7.2 (3H,m), 7.5–7.8 (1H,m), 9.9 (1H, broad s).

DESCRIPTION 16

2-Amino-1-methylindole-3-carboxylic acid, methyl ester (D16)

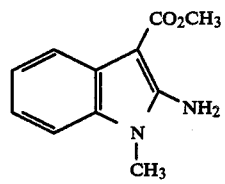

The amino ester (D15) (9.5 g; 50 mM) was dissolved in dry dimethylformamide (44 ml) and added dropwise to a stirred suspension of 80% sodium hydride (1.97 g; 65 mM) in dry dimethylformamide (37 ml) at 0° under N$_2$. The solution was then stirred for a further 30 minutes, then methyl iodide (8.9 g) in dimethylformamide (8 ml) added. Stirring was continued for 3 h, then the reaction mixture poured onto iced water (500 ml). The resultant brown precipitate was filtered, washed with water and dried. Recrystallisation from methanol afforded the title compound as brown needles (4.5 g; 44%), m.p. 192°–196°.

NMR (CDCl$_3$)δ: 3.25 (3H,s), 3.85 (3H,s), 6.80 (2H, broad s), 6.90–7.20 (3H,m), 7.60–7.80 (1H,m).

Observed M+ 204.0902.
C$_{11}$H$_{12}$N$_2$O$_2$ requires: 204.0899.
Found: C, 66.63; H, 4.86; N, 10.00%. C$_{15}$H$_{14}$N$_2$O$_3$ requires: C, 66.66; H, 5.22; N, 10.36%.

DESCRIPTION 17

2,9-Dimethyl-4-hydroxy-9H-pyrido[2,3-b]indole-3-carboxylic acid, methyl ester (D17)

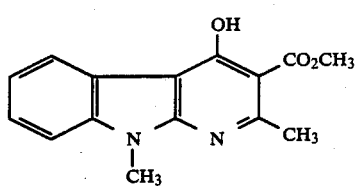

A solution of the aminoester (D16) (5.4 g; 26.5 mM), methyl β-methoxycrotonate (6.89 g; 53 mM) and paratoluenesulphonic acid (0.25 g; 1.3 mM) in toluene was refluxed with distillation for 2 h, during which time 60 ml distillate was collected. The brown solution was then cooled, and 1M sodium methoxide in methanol (31 ml; 31 mM) was added. The solution was then refluxed for a further 3 h, with the removal of 30 ml distillate. The solution was cooled, and the brown precipitate collected by filtration. The solid obtained (5 g) was dissolved in methanol (30 ml), and acetic acid (1.2 g) in methanol (5 ml) added, followed by water (500 ml). The white solid was filtered, washed with water and dried to afford the title compound (3.6 g; 50%).

Recrystallisation from methanol afforded analytical material, m.p. 174°–176°.

NMR (DMSO)δ: 2.72 (3H,s), 3.86 (3H,s) 3.92 (3H,s), 7.25–7.65 (3H,m), 8.10 (1H,m), 12.25 (1H, broad s).

Observed M+ 270.1008.

$C_{15}H_{14}N_2O_3$ requires: 270.1005.

Found: C, 66.63; H, 4.86; N, 10.00%. $C_{15}H_{14}N_2O_3$ requires: C, 66.66; H, 5.22; N, 10.36%.

DESCRIPTION 18

4-Chloro-2,9-dimethyl-9H-pyrido[2,3-b]indole-3-carboxylic acid, methyl ester (D18)

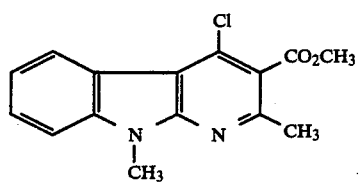

(D18)

A solution of the hydroxyester (D17) (3 g; 11.1 mM) in phosphorus oxychloride (45 ml) was refluxed for 3 h. The solution was then cooled, and evaporated to dryness. The black residue was partitioned between dichloromethane and aqueous sodium bicarbonate, with cooling. The organic layer was washed with brine, dried and evaporated to afford a dark brown solid (3.3 g) which was chromatographed on $SiO_2$ (100 g) with dichloromethane elution. The appropriate fractions were combined and evaporated to dryness to afford a white solid (2.1 g; 66%). Recrystallisation from methanol afforded the title compound as white needles, m.p. 110°–111°.

NMR $(CDCl_3)\delta$: 2.75 (3H,s), 3.98 (3H,s), 4.06 (3H,s), 7.25–7.75 (3H,m), 8.40–8.55 (1H,m).

Observed M+ 288.0669.

$C_{15}H_{13}N_2O_2Cl$ requires: 288.0666.

Found: C, 62.59; H, 4.67; N, 9.78%. $C_{15}H_{13}N_2O_2Cl$ requires: C, 62.40; H, 4.54; N, 9.70%.

DESCRIPTION 19

4-Amino-2-methyl-9H-pyrido[2,3-b]indole-3-carboxamide (D19)

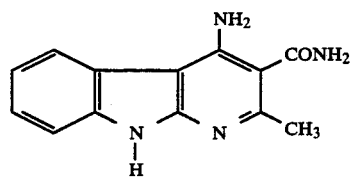

(D19)

The amino acid (D4) (3.18 g; 11.5 mM) was added slowly to thionyl chloride (45 ml) at 0°. The stirred suspension was refluxed for 6 h, allowed to cool, then evaporated to dryness. The residue was cooled in a dry ice/acetone bath and approximately 80 ml liquid ammonia added, with vigorous stirring. After ammonia had evaporated, water (120 ml) was added and the residue stirred vigorously for 1 hr. Filtration afforded the title compound as a brown solid (2.5 g; 91%), m.p. 305°–308°.

NMR (DMSO)$\delta$: 2.53 (3H, s), 6.25 (2H, s), 7.00–7.75 (5H, m), 8.15–8.30 (1H, m), 10.50–12.50 (1H, s).

DESCRIPTION 20

2-Amino-1-methylindole-3-carboxylic acid, ethyl ester (D20)

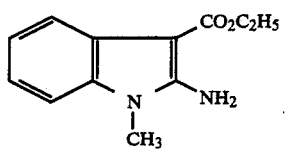

(D20)

The title compound was prepared, using a method similar to that described in Descriptions 14, 15 and 16, from ethyl cyanoacetate.

m.p. 132°–134°.

DESCRIPTION 21

4-Chloro-2,9-dimethyl-9H-pyrido[2,3-b]indole-3-carboxylic acid, ethyl ester (D21)

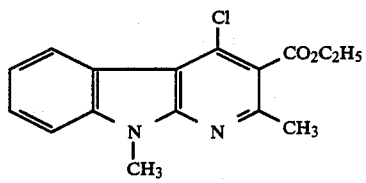

(D21)

The title compound was prepared from the amino ester (D20) and ethyl $\beta$-ethoxycrotonate using a method similar to that outlined in Descriptions 17 and 18.

m.p. 123°–123.5°.

DESCRIPTION 22

2-Amino-1-methyl-1H-indole-3-carbonitrile (D22)

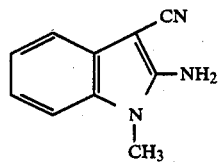

(D22)

To a solution of 2-amino-1H-indole-3-carbonitrile (EP 0107193A1) (20.0 g 12.7 mM) in DMF (100 ml) at ca. 5° and under an atmosphere of nitrogen, was added potassium tert-butoxide (14.59 g, 12.7 mmol) portionwise over 5 minutes. The cooling bath was removed and the whole stirred at room temperature for 30 minutes. The whole was then recooled and methyl iodide (8 ml, 12.7 mM), dissolved in DMF (20 ml), added dropwise such that the temperature remained below 5°. After a further 40 minutes at this temperature, water (500 ml) was added dropwise and the resulting solid collected by filtration, washed with water and dried under reduced pressure to give the title compound (D3) (13.08 g, 60%) as a brown solid.

NMR $(D_6DMSO)\delta$: 3.63 (3H, s), 7.00–7.20 (4H, m), 7.21–7.40 (2H, m).

EXAMPLE 1

4-Amino-2-methyl-9H-pyrido[2,3-b]indole-3-carboxylic acid, methyl ester (E1)

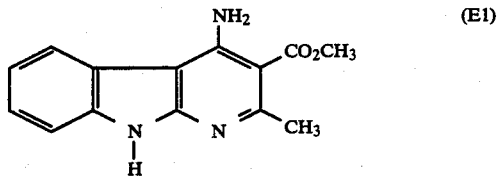

The amino acid (D4) (3 g; 10.8 mM) was added slowly to thionyl chloride (60 ml) at 0°. The stirred suspension was refluxed for 6 h, allowed to cool, then evaporated to dryness. The residue was cooled in an ice-bath, and a 1M solution of sodium methoxide in methanol (70 ml) added. The suspension was stirred vigorously at room temperature for approximately 16 h, then poured onto water (300 ml) and the pH adjusted to 7 using 5M hydrochloric acid. The brown solid was filtered and washed well with water. Recrystallisation from methanol afforded 1.3 g brown needles which were further recrystallised with charcoal treatment from methanol to give the title compound (0.8 g; 30%) as white needles, m.p. 256°–266° (decomposition).

NMR (DMSO)δ: 2.66 (3H, s), 3.90 (3H, s), 7.20 (2H, s, ex D$_2$O), 7.10–7.55 (3H, m), 8.35 (1H, m), 11.71 (1H, s, ex D$_2$O).

Observed M+ 255.0999.

$C_{14}H_{13}N_3O_2$ requires 255.1008.

EXAMPLE 1

Alternative Procedure

4-Amino-2-methyl-9H-pyrido[2,3-b]indole-3-carboxylic acid, methyl ester (E1)

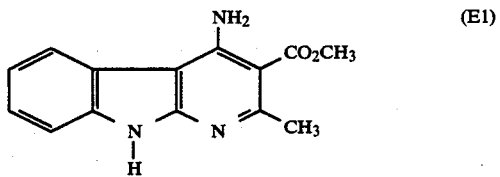

A mixture of the intermediate (D7) (11.34 g; 30 mM), anisole (9.53 ml), trifluoroacetic acid (96 ml) and concentrated sulphuric acid (4.76 ml) was stirred at room temperature for 1.5 h. The solution was then added dropwise to vigorously stirred saturated aqueous sodium bicarbonate (2 liters), with ice cooling. The resulting suspension was kept at 5° for 16 h, then filtered. The white solid was washed thoroughly with water, cold methanol and finally cold ether, then dried to afford the title compound (7.31 g; 88%). The solid was then extracted with boiling methanol in a Soxhlet apparatus for 16 h. After cooling, the resultant white product was filtered off, and dried at 60° in vacuo to afford analytically pure material (5.58 g; 67%).

Found: C, 65.61; H, 5.09; N, 16.25. $C_{14}H_{13}N_3O_2$ requires: C, 65.87; H, 5.13; N, 16.46%.

EXAMPLE 2

4-Amino-2,9-dimethyl-9H-pyrido[2,3-b]indole-3-carboxylic acid, methyl ester (E2)

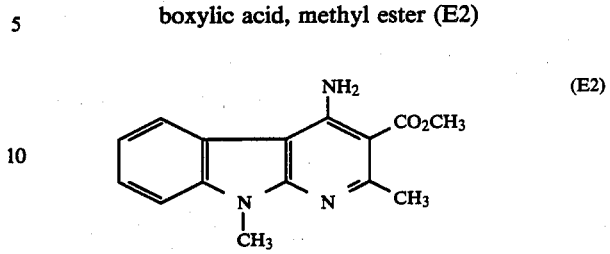

A solution of E1 (0.889 g; 3.5 mM) in dry dimethylformamide (10 ml) was added dropwise to a stirred suspension of 80% sodium hydride (0.115 g; 3.85 mM) in dimethylformamide (5 ml) at 0° under N$_2$. After 0.5 h, methyl iodide (0.564 g; 4.3 mM) in dimethylformamide was added, and the solution allowed to stir at room temperature for approximately 16 h. The solution was then poured onto water and extracted twice with dichloromethane. The combined organic phase was washed well with water, dried and evaporated to give a yellow solid (0.9 g). Recrystallisation from ethanol afforded the title compound as beige crystals (0.5 g; 53%), m.p. 98°–100°.

NMR (CDCl$_3$)δ: 2.85 (3H, s), 3.91 (3H, s), 3.98 (3H, s), 6.50–6.90 (2H, s, ex D$_2$O), 7.20–7.50 (3H, m), 7.75–7.90 (1H, m).

Observed M+ 269.1169.

$C_{15}H_{15}N_3O_2$ requires 269.1164.

Found: C, 66.90; H, 5.50; N, 15.52. $C_{15}H_{15}N_3O_2$ requires C, 66.90; H, 5.61; N, 15.60%.

EXAMPLE 3

4-Amino-2-methyl-9H-pyrido[2,3-b]indole-3-carboxylic acid, ethyl ester (E3)

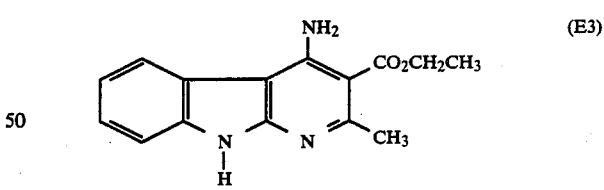

The title compound was prepared from the intermediate (D9) in 88% yield using a procedure similar to that in Example 1, Alternative Procedure. Product was obtained as white needles after Soxhlet extraction with ethanol. m.p. 253°–4° C.

NMR (DMSO)δ: 1.35 (3H,t,J=8), 2.66 (3H,s), 4.35 (2H, q,J=8), 7.23–7.47 (5H,m), 8.27 (1H,m), 11.70 (1H, broad s).

Observed M+ 269.1182.

$C_{15}H_{15}N_3O_2$ requires: 269.1164.

Found: C, 66.76; H, 5.60; N, 15.52. $C_{15}H_{15}N_3O_2$ requires: C, 66.90; H, 5.61; N, 15.60%.

EXAMPLE 4

4-Amino-2,9-dimethyl-9H-pyrido[2,3-b]indole-3-carboxylic acid, ethyl ester (E4)

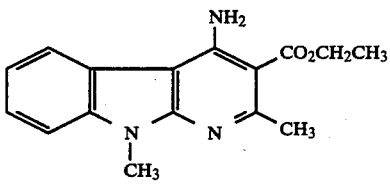

The title compound was prepared from the ethyl ester E3 (5.72 g; 21 mM) using a method similar to that described in Example 2. Recrystallisation from ethanol afforded white crystals (2.21 g; 37%).

m.p. 79°-80°.

NMR (CDCl$_3$)δ: 1.35-1.53 (3H,t,J=8), 2.75 (3H,s), 3.90 (3H,s), 4.28-5.55 (2H,q,J=8), 6.68 (2H, broad s), 7.18-7.48 (3H,m), 7.78-7.88 (1H,m).

Observed M+ 283.1330.

C$_{16}$H$_{17}$N$_3$O$_2$ requires: 283.1321.

Found: C, 67.80; H, 6.08; N, 14.79. C$_{16}$H$_{17}$N$_3$O$_2$ requires: C, 67.83; H, 6.05; N, 14.83%.

EXAMPLE 4

(Alternative Procedure)

4-Amino-2,9-dimethyl-9H-pyrido[2,3-b]indole-3-carboxylic acid, ethyl ester (E4)

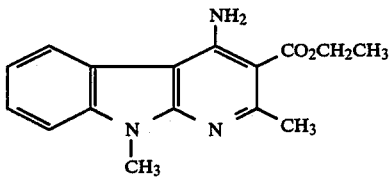

The title compound was prepared from 2-amino-1-methyl-1H-indole-3-carbonitrile (D22) and ethyl acetoacetate using a method similar to that described in Description 2.

m.p. 95°.

EXAMPLE 5

4-Amino-6-chloro-2,9-dimethyl-9H-pyrido[2,3-b]indole-3-carboxylic acid, methyl ester (E5)

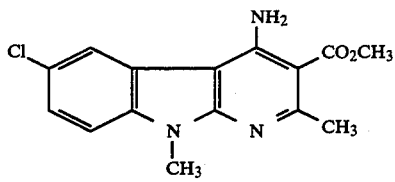

The title compound was prepared from the ester E1 by direct chlorination using standard conditions followed by methylation using a method similar to that described in Example 2.

m.p. 203°-211°.

Found: C, 59.76; H, 4.75; N, 13.93. C$_{15}$H$_{14}$N$_3$O$_2$Cl requires: C, 59.31; H, 4.65; N, 13.83%.

EXAMPLE 6

4-Amino-9-methyl-2-phenyl-9H-pyrido[2,3-b]indole-3-carboxylic acid, methyl ester (E6)

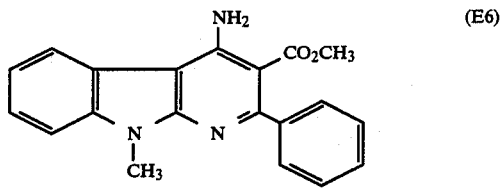

The title compound (E6) was prepared in 32% overall yield from the intermediate (D12) using a method similar to that outlined in Description 7 and Examples 1, Alternative Procedure, and 2.

m.p. 168°-70° (from ether).

NMR (CDCl$_3$)δ 3.46 (3H, s), 3.95 (3H, s), 6.35 (2H, s, ex D$_2$O), 7.30-7.65 (8H, m) and 7.88 (1H, dd, J=7, 1).

Found: C, 72.43; H, 5.16; N, 12.65. C$_{20}$H$_{17}$N$_3$O$_2$ requires C, 72.49; H, 5.17 and N, 12.68%.

EXAMPLE 7

4-n-Butylamino-2,9-dimethyl-9H-pyrido[2,3-b]indole-3-carboxylic acid, methyl ester (E7)

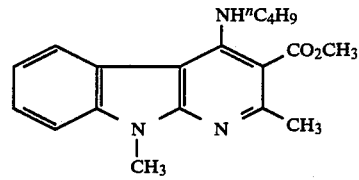

A solution of the chloroester (D18) (1 g; 3.5 mM) in n-butylamine (20 ml) was refluxed for 3 h. The solution was then cooled and evaporated to dryness. The residue was partioned between dichloromethane and water, and the organic layer washed with brine, dried and evaporated to afford a yellow oil (1 g).

Recrystallisation from methanol gave the title compound as white needles (0.6 g; 53%), m.p. 68°-69°.

NMR (CDCl$_3$)δ 0.90 (3H, t, J=10), 1.10-1.75 (4H, m), 2.70 (3H, s), 3.35-3.65 (2H, m), 3.90 (3H, s), 3.94 (3H, s), 6.50 (1H, broad s), 7.15-7.50 (3H, m), 7.80-7.95 (1H, m).

Observed M+ 325.1779.

C$_{19}$H$_{23}$N$_3$O$_2$ requires 325.1781.

Found C, 70.25; H, 7.23; N, 13.05. C$_{19}$H$_{23}$N$_3$O$_2$ requires C, 70.13; H, 7.12; N, 12.91%.

EXAMPLE 8

2,9-Dimethyl-4-methylamino-9H-pyrido[2,3-b]indole-3-carboxylic acid, methyl ester (E8)

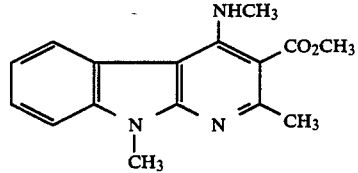

A solution of the chloroester (D18) (2 g; 6.93 mM) in methanol (60 ml) containing ca. 17 g methylamine was heated in a stainless steel bomb for 17 h at 100°. The resultant solution was evaporated to dryness, then dissolved in dichloromethane, washed with brine, dried and evaporated to give a yellow solid (1.6 g). Chromatography on silica (100 g) using 5% ethyl acetate-pentane increasing to 25% ethyl acetate-pentane afforded 1.3 g pale yellow solid. Recrystallisation from methanol afforded the title compound as a white solid (0.86 g; 44%).

m.p. 90°-91°

NMR (CDCl$_3$)δ 2.74 (3H, s), 3.21 (3H, d, J=6), 3.91 (3H, s), 3.96 (3H, s), 6.55 (1H, broad s), 7.1–7.5 (3H, m), 7.92 (1H, m).

Observed M+ 283.1322.

$C_{16}H_{17}N_3O_2$ requires 283.1321.

Found: C, 67.51; H, 6.17; N, 15.00. $C_{16}H_{17}N_3O_2$ requires C, 67.83; H, 6.05; N, 14.83%.

EXAMPLE 9

2,9-Dimethyl-4-dimethylamino-9H-pyrido[2,3-b]indole-3-carboxylic acid, methyl ester (E9)

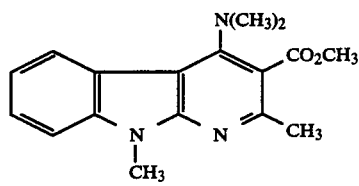

The title compound was prepared in 20% yield from the chloroester (D18) and dimethylamine using a procedure similar to that described in Example 8. Product was obtained as white needles after recrystallisation from methanol.

m.p. 106.5°-108°.

NMR (CDCl$_3$)δ 2.65 (3H, s), 3.08 (6H, s), 3.93 (3H, s), 3.98 (3H, s), 7.2–7.55 (3H, m), 7.95–8.15 (1H, m).

Observed M+ 297.1474.

$C_{17}H_{19}N_3O_2$ requires 297.1477.

Found: C, 68.41; H, 6.78; N, 13.97. $C_{17}H_{19}N_3O_2$ requires C, 68.67; H, 6.44; N, 14.13%.

EXAMPLE 10

4-Amino-2-methyl-9H-pyrido[2,3-b]indole-3-carboxylic acid, 2-propenyl ester (E10)

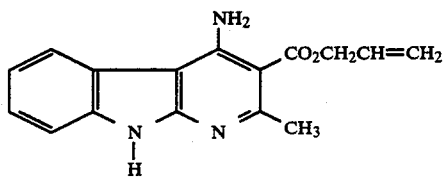

The title compound was prepared from the ester D13 using a method similar to that described in Example 1, Alternative Procedure.

m.p. 220°-222°.

NMR (d$_6$-DMSO)δ 2.70 (3H, s), 4.75–4.95 (2H, d, J=4), 5.20–5.60 (2H, m), 5.90–6.40 (1H, m), 7.00–7.60 (5H, m), 8.15–8.45 (1H, m), 11.75 (1H, broad s).

Observed M+ 281.1161.

$C_{16}H_{15}N_3O_2$ requires 281.1164.

Found: C, 68.28; H, 5.36; N, 14.94. $C_{16}H_{15}N_3O_2$ requires C, 68.31; H, 5.37; N, 14.94%.

EXAMPLE 11

4-Amino-2,9-dimethyl-9H-pyrido[2,3-b]indole-3-carboxylic acid, 2-propenyl ester (E11)

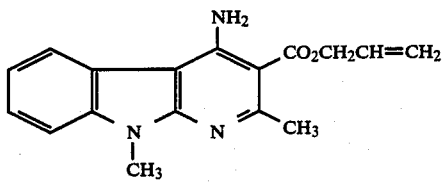

The title compound was prepared from ester E10 using a method similar to that described in Example 2.

m.p. 94° (from methanol).

NMR (CDCl$_3$)δ 2.85 (3H, s), 3.90 (3H, s), 4.75–4.95 (2H, m), 5.20–5.60 (2H, m), 5.85–6.40 (1H, m), 6.70 (2H, broad s), 7.20–7.55 (3H, m), 7.75–7.90 (1H, m).

Observed M+ 295.1325.

$C_{17}H_{17}N_3O_2$ requires 295.1320.

Found: C, 69.12; H, 5.97; N, 14.32. $C_{17}H_{17}N_3O_2$ requires C, 69.14; H, 5.80; N, 14.23%.

EXAMPLE 12

4-Amino-9-ethyl-2-methyl-9H-pyrido[2,3-b]indole-3-carboxylic acid, methyl ester (E12)

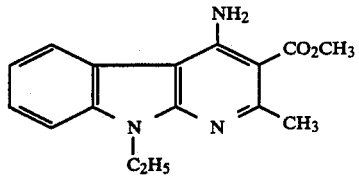

The title compound was prepared from the ester E1 and ethyl iodide using a method similar to that described in Example 2.

m.p. 108°-110° (from diethyl ether).

NMR (CDCl$_3$)δ 1.43 (3H, t, J=7), 2.82 (3H, s), 3.84 (3H, s), 4.48 (2H, q, J=7), 6.67 (2H, broad s), 7.15–7.5 (3H, m), 7.85 (1H, dd, J=6, 2).

Observed M+ 283.1324.

$C_{16}H_{17}N_3O_2$ requires 283.1321.

Found: C, 67.98; H, 6.15; N, 15.06. $C_{16}H_{17}N_3O_2$ requires C, 67.83; H, 6.05; N, 14.83%.

EXAMPLE 13

4-Amino-2-methyl-9-(2-propenyl)-9H-pyrido[2,3-b]indole-3-carboxylic acid, methyl ester (E13)

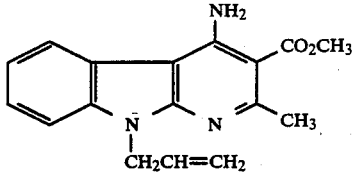

The title compound was prepared from the ester E1 and allyl bromide using a method similar to that described in Example 2.

m.p. 78°-85° (from diethyl ether).

NMR (CDCl$_3$)δ 2.88 (3H, s), 3.96 (3H, s), 5.1 (4H, m), 5.8–6.3 (1H, m), 6.7 (2H, broad s), 7.4 (3H, m), 7.85 (1H, dd, J 6, 2).

Observed M+ 295.1325.
C$_{17}$H$_{17}$N$_3$O$_2$ requires 295.1320.
Found C, 69.24; H, 5.99; N, 14.06. C$_{17}$H$_{17}$N$_3$O$_2$ requires C, 69.14; H, 5.80; N, 14.23%.

EXAMPLE 14

4-Amino-2,9-dimethyl-9H-pyrido[2,3-b]indole-3-carboxylic acid, 2-propynyl ester (E14)

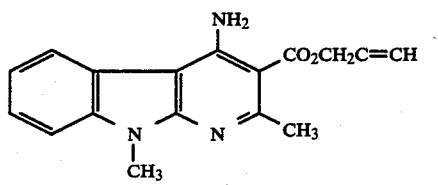

(E14)

The title compound was prepared in 85% yield from the acid (D11) and propargyl bromide using a procedure similar to that described in Description 13. Product was obtained as white needles after recrystallisation from methanol.

m.p. 164°–165°.

NMR (d$_6$-DMSO) δ 2.70 (3H, s), 3.55–3.65 (1H, t, J=3), 3.85 (3H, s), 5.00–5.05 (2H, d, J=3), 7.1–7.7 (5H, m), 8.30–8.45 (1H, broad d, J=8).

Observed M+ 293.1164.
C$_{17}$H$_{15}$N$_3$O$_2$ requires 293.1164.
Found: C, 69.53; H, 5.32; N, 14.18. C$_{17}$H$_{15}$N$_3$O$_2$ requires C, 69.61; H, 5.15; N, 14.33%.

The following compounds (E15–E33) were prepared in accordance with the invention using methods similar to those illustrated by the invention.

EXAMPLE 15

4-Amino-2-methyl-9H-pyrido[2,3-b]indole-3-carboxylic acid, n-propyl ester (E15)

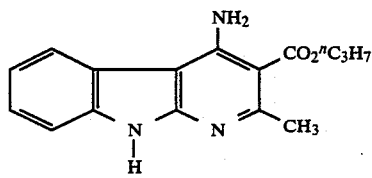

(E15)

m.p. 223°–6°.
Found: C, 67.81; H, 6.01; N, 14.64. C$_{16}$H$_{17}$N$_3$O$_2$ requires C, 67.83; H, 6.05; N, 14.83%.

EXAMPLE 16

4-Amino-2-methyl-9-n-pentyl-9H-pyrido[2,3-b]indole-3-carboxylic acid, methyl ester (E16)

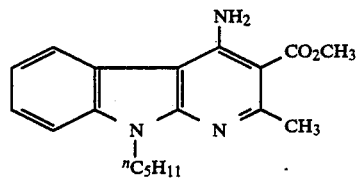

(E16)

m.p. 96°–97°.
Found: C, 70.01; H, 7.26; N, 12.52. C$_{19}$H$_{23}$N$_3$O$_2$ requires C, 70.13; H, 7.12; N, 12.91%.

EXAMPLE 17

4-Amino-2-methyl-9-(2-propynyl)-9H-pyrido[2,3-b]indole-3-carboxylic acid, methyl ester (E17)

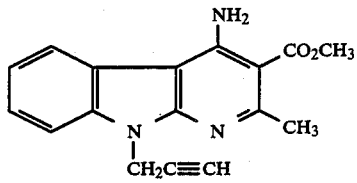

(E17)

m.p. 187°–188°.
Found: C, 69.60; H, 5.09; N, 14.29. C$_{17}$H$_{15}$N$_3$O$_2$ requires C, 69.61; H, 5.15; N, 14.33%.

EXAMPLE 18

4-Diacetylamino-2,9-dimethyl-9H-pyrido[2,3-b]indole-3-carboxylic acid, methyl ester (E18)

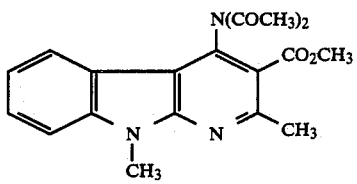

(E18)

m.p. 154°–5°.
Found: C, 63.48; H, 5.60; N, 11.64. C$_{19}$H$_{19}$N$_3$O$_4$ requires C, 64.58; H, 5.42; N, 11.89%.

EXAMPLE 19

4-Acetylamino-2,9-dimethyl-9H-pyrido[2,3-b]indole-3-carboxylic acid, methyl ester (E19)

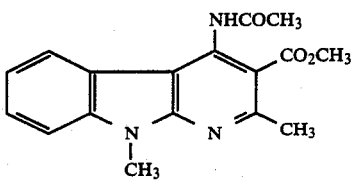

(E19)

m.p. 215°–19°.
Found: C, 65.67; H, 5.73; N, 13.55. C$_{17}$H$_{17}$N$_3$O$_3$ requires C, 65.58; H, 5.50; N, 13.50%.

EXAMPLE 20

4-Amino-7-chloro-2,9-dimethyl-9H-pyrido[2,3-b]indole-3-carboxylic acid, methyl ester (E20)

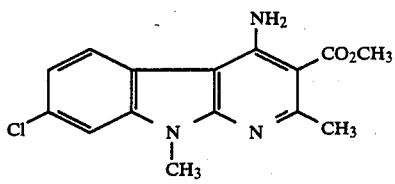

(E20)

m.p. 160°–5°.
Found: C, 58.9; H, 4.6; N, 13.5. C$_{15}$H$_{14}$N$_3$O$_2$Cl requires C, 59.3; H, 4.65; N, 13.8%.

EXAMPLE 21

4-Amino-7-chloro-2-methyl-9H-pyrido[2,3-b]indole-3-carboxylic acid, methyl ester (E21)

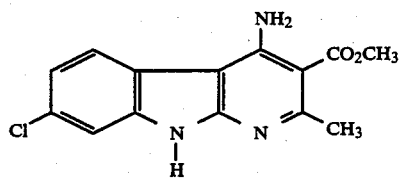

m.p. 303°-7°.
Found C, 58.04; H, 4.10; N, 14.29. $C_{14}H_{12}N_3O_2Cl$ requires C, 58.04; H, 4.18; N, 14.50%.

EXAMPLE 22

4-Amino-6-chloro-2-methyl-9H-pyrido[2,3-b]indole-3-carboxylic acid, methyl ester (E22)

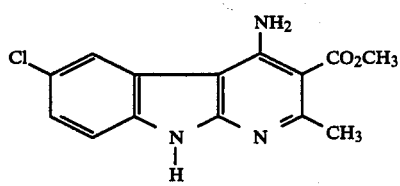

m.p. 329°-30°.
Found, C, 58.08; H, 4.33; N, 14.44. $C_{14}H_{12}N_3O_2Cl$ requires C, 58.04; H, 4.18; N, 14.50%.

EXAMPLE 23

4-Amino-2-phenyl-9-(2-propenyl)-9H-pyrido[2,3-b]indole-3-carboxylic acid, methyl ester (E23)

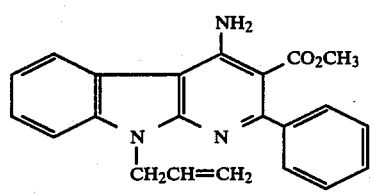

m.p. 101°-3°.
Found: C, 74.25; H, 5.07; N, 11.70. $C_{22}H_{19}N_3O_2$ requires C, 73.93; H, 5.36; N, 11.76%.

EXAMPLE 24

4-Amino-2,9-dimethyl-9H-pyrido[2,3-b]indole-3-carboxylic acid, n-propyl ester (E24)

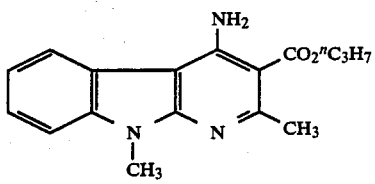

m.p. 82°-3°.
Found: C, 68.74; H, 6.70; N, 13.95. $C_{17}H_{19}N_3O_2$ requires C, 68.67; H, 6.44; N, 14.13%.

EXAMPLE 25

4-Amino-2,9-dimethyl-6-hydroxy-9H-pyrido[2,3-b]indole-3-carboxylic acid, methyl ester (E25)

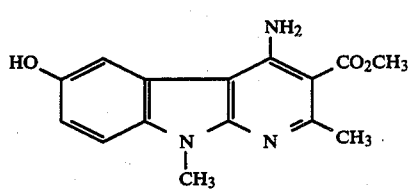

m.p. 187°-91°.

EXAMPLE 26

4-Amino-2,9-dimethyl-9H-pyrido[2,3-b]indole-3-carboxylic acid, cyclopropylmethyl ester (E26)

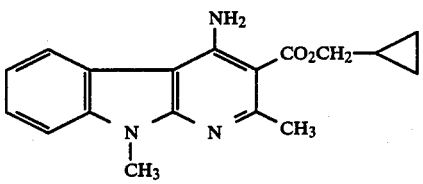

m.p. 89°-90°.
Found: C, 69.91; H, 6.27; N, 13.39. $C_{18}H_{19}N_3O_2$ requires C, 69.88; H, 6.19; N, 13.58%.

EXAMPLE 27

4-Amino-2-methyl-9-(2-propenyl)-9H-pyrido[2,3-b]indole-3-carboxylic acid, 2-propenyl ester (E27)

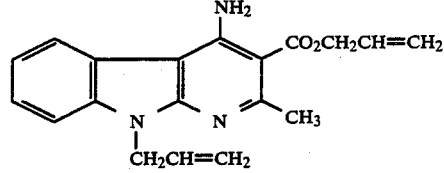

m.p. 110°-113°.
Found: C, 71.04; H, 6.04; N, 12.71. $C_{19}H_{19}N_3O_2$ requires: C, 71.01; H, 5.96; N, 13.08%.

EXAMPLE 28

2,9-Dimethyl-4-ethylamino-9H-pyrido[2,3-b]indole-3-carboxylic acid, methyl ester (E28)

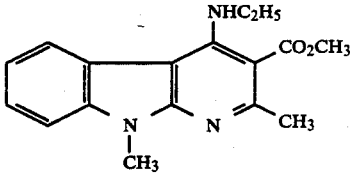

m.p. 105.5°-107°.
Found: C, 68.59; H, 6.53; N, 13.99. $C_{17}H_{19}N_3O_2$ requires: C, 68.67; H, 6.44; N, 14.13%.

EXAMPLE 29

4-Amino-9-ethyl-2-methyl-9H-pyrido[2,3-b]indole-3-carboxylic acid, ethyl ester (E29)

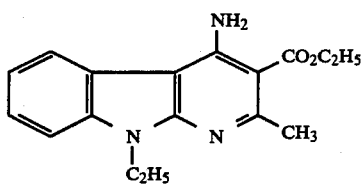

m.p. 112°–113°.

Found: C, 67.65; H, 6.51; N, 13.94. $C_{17}H_{19}N_3O_2$ requires: C, 68.67; H, 6.44; N, 14.13%.

EXAMPLE 30

4-Amino-9-cyclopropylmethyl-2-methyl-9H-pyrido[2,3-b]indole-3-carboxylic acid, methyl ester (E30)

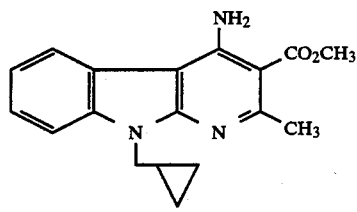

m.p. 123°–125°.

Found: C, 70.04; H, 6.29; N, 13.44. $C_{18}H_{19}N_3O_2$ requires: C, 69.88; H, 6.19; N, 13.58%.

EXAMPLE 31

4-Amino-9-cyclopropylmethyl-2-methyl-9H-pyrido[2,3-b]indole-3-carboxylic acid, ethyl ester (E31)

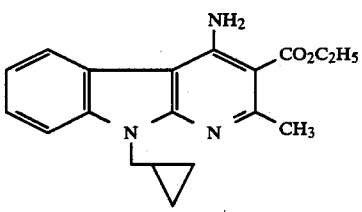

m.p. 115°–116°.

Found: C, 70.46; H, 6.44; N, 12.87. $C_{19}H_{21}N_3O_2$ requires: C, 70.57; H, 6.55; N, 12.99%.

EXAMPLE 32

2,9-Dimethyl-4-methylamino-9H-pyrido[2,3-b]indole-3-carboxylic acid, ethyl ester, (Z)-2-butenedioate (E32)

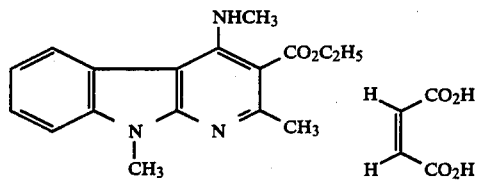

m.p. 155°–157°.

Found: C, 60.65; H, 5.64; N, 10.16. $C_{21}H_{23}N_3O_6$ requires: C, 61.00; H, 5.61; N, 10.16%.

EXAMPLE 33

4-Amino-2-ethyl-9-methyl-9H-pyrido[2,3-b]indole-3-carboxylic acid, methyl ester (E33)

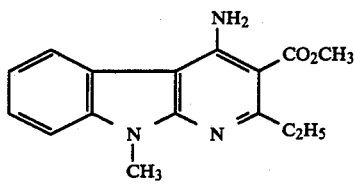

m.p. 108°–109°.

Found: C, 66.93; H, 6.09; N, 14.61. $C_{16}H_{17}N_3O_2$ requires: C, 67.83; H, 6.05; N, 14.83%.

PHARMACOLOGICAL DATA

Geller-Seifter Procedure

Potential anxiolytic properties have been evaluated using the Geller-Seifter procedure based on that originally described by Geller and Seifter, (1960) Psychopharmacologia, 1, 482–492. This procedure has been shown to be selective for drugs with anxiolytic properties (Cook and Sepinwall, (1975) "Mechanism of Action of Benzodiazepines" ed. Costa, E. and Greengard, P., Raven Press, New York, pp. 1–28).

Rats are trained on a variable interval 30 sec schedule (VI30) to press a lever in order to obtain food reward. The 5 min sessions of the VI30 schedule alternate with 2–5 min of a schedule (FR5) in which every 5th lever press is followed by presentation of a food pellet paired with a 0.5 sec mild footshock. The total study lasts approximately 30 mins. Rats typically respond with high rates of lever pressing under the VI30 schedule and low response rates under the FR5 'conflict' session. Anxiolytic drugs increase the suppressed response rates of rats in a 'conflict' session.

Drugs are administered intraperitoneally or orally to groups of 3–8 rats 30 min before testing.

The results are expressed as the percentage increase in square root of the total number of lever presses in the FR5 'conflict' session. Square root transformation is necessary to normalise the data for statistical analysis using parametric methods.

Testing Results

The following compounds have shown activity in the above test as detailed in the Table.

| Compound | dose mg/kg | increase in responding in the 'conflict' session |
|---|---|---|
| Example 1 (E1) | 50 po | +143% |
| Example 2 (E2) | 50 po | +50% |
| Example 4 (E4) | 50 po | +73% |
| Example 8 (E8) | 50 po | +112% |
| Example 11 (E11) | 50 po | +138% |
| Example 13 (E13) | 20 ip | +81% |
| Example 14 (E14) | 50 po | +102% |
| Example 24 | 50 po | +78% |

-continued

| Compound | dose mg/kg | increase in responding in the 'conflict' session |
|---|---|---|
| (E24) Example 26 (E26) | 50 po | +57% |
| Example 29 (E29) | 20 po | +27% |

We claim:

1. A compound of formula (I) or a pharmaceutically acceptable salt thereof:

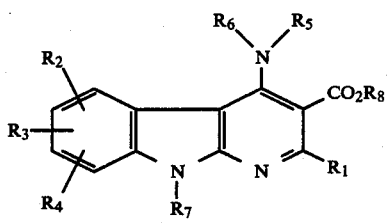

wherein:
$R_1$ is hydrogen, $C_{1-6}$ alkyl, phenyl or phenyl $C_{1-4}$ alkyl wherein the phenyl moiety is optionally substituted by one or more $C_{1-6}$ alkyl, $C_{1-6}$ alkoxy, $C_{1-6}$ alkylthio, hydroxy, $C_{2-7}$ alkanoyl, halo, trifluoromethyl, nitro, amino optionally substituted by one or two $C_{1-6}$ alkyl groups or by $C_{2-7}$ alkanoyl, cyano, carbamoyl or carboxy groups;

$R_2$, $R_3$ and $R_4$ are independently selected from hydrogen, $C_{1-6}$ alkyl, $C_{1-6}$ alkoxy, $C_{1-6}$ alkoxycarbonyl, $C_{1-6}$ alkylthio, hydroxy, $C_{2-7}$ alkanoyl, chloro, fluoro, trifluoromethyl, nitro, amino optionally substituted by one or two $C_{1-6}$ alkyl groups or by $C_{2-7}$ alkanoyl, cyano, carbamoyl and carboxy, and phenyl, phenyl $C_{1-4}$ alkyl or phenyl $C_{1-4}$ alkoxy in which any phenyl moiety is optionally substituted by $C_{1-6}$ alkyl, $C_{1-6}$ alkoxy, $C_{1-6}$ alkoxycarbonyl, $C_{1-6}$ alkylthio, hydroxy, $C_{2-7}$ alkanoyl, chloro, fluoro, trifluoromethyl, nitro or amino optionally substituted by one or two $C_{1-6}$ alkyl groups or by $C_{2-7}$ alkanoyl, cyano, carbamoyl and carboxy;

$R_5$ and $R_6$ are independently selected from hydrogen, $C_{1-6}$ alkyl, $C_{3-7}$ cycloalkyl, $C_{3-7}$ cycloalkyl-$C_{1-4}$ alkyl, $C_{2-6}$ alkenyl, $C_{1-7}$ alkanoyl, $C_{1-6}$ alkylsulphonyl, di-($C_{1-6}$ alkyl)amino $C_{1-6}$ alkyl, 3-oxobutyl, 3-hydroxybutyl, phenyl, phenyl $C_{1-4}$ alkyl, benzoyl, phenyl $C_{2-7}$ alkanoyl or benzenesulphonyl any of which phenyl moieties are optionally substituted by one or two halogen, $C_{1-6}$ alkyl, $C_{1-6}$ alkoxy, $CF_3$, amino or carboxy, or $R_5$ and $R_6$ together form —$(CH_2)_4$—, —$(CH_2)_5$—, —$(CH_2)_2$—O—$(CH_2)_2$— or —$(CH_2)_2$—$NR_9$—$(CH_2)_2$— wherein $R_9$ is hydrogen or $C_{1-6}$ alkyl optionally substituted by hydroxy;

$R_7$ is hydrogen, $C_{1-6}$ alkyl, $C_{3-6}$ cycloalkyl, $C_{3-6}$ cycloalkyl-$C_{1-4}$ alkyl, $C_{2-6}$ alkenyl or $C_{2-6}$ alkylnyl; and —$CO_2R_8$ is a pharmaceutically acceptable ester group, wherein $R_8$ is $C_{1-6}$ alkyl, $C_{2-6}$ alkenyl, $C_{2-6}$ alkynyl, $C_{3-6}$ cycloalkyl or $C_{3-6}$ cycloalkyl-$C_{1-4}$ alkyl.

2. A compound according to claim 1 wherein $R_8$ is $C_{1-6}$ alkyl, $C_{2-6}$ alkenyl, $C_{2-6}$ alkynyl or $C_{3-6}$ cycloalkyl-$C_{1-4}$ alkyl.

3. A compound according to claim 1 wherein $R_1$ is hydrogen, $C_{1-3}$ alkyl, phenyl or benzyl.

4. A compound according to claim 1 wherein one of $R_2$, $R_3$ and $R_4$ is hydrogen, chloro or hydroxy and the remainder are hydrogen.

5. A compound according to claim 1 wherein $R_5$ and $R_6$ are independently hydrogen, $C_{1-6}$ alkyl or $C_{1-7}$ alkanoyl.

6. A compound according to claim 1 wherein $R_7$ is hydrogen, $C_{1-6}$ alkyl, $C_{2-6}$ alkenyl or $C_{2-6}$ alkynyl.

7. A compound according to claim 1 wherein $R_1$ is methyl, $R_2$, $R_3$ and $R_4$ are each hydrogen, $R_5$ and $R_6$ are independently hydrogen or methyl, $R_7$ is hydrogen, methyl, ethyl or prop-2-enyl and $R_8$ is methyl, ethyl, propyl, prop-2-enyl or prop-2-ynyl.

8. 4-Amino-2-methyl-9H-pyrido[2,3-b]indole-3-carboxylic acid, methyl ester,
4-amino-2,9-dimethyl-9H-pyrido[2,3-b]indole-3-carboxylic acid, methyl ester,
4-amino-2-methyl-9H-pyrido[2,3-b]indole-3-carboxylic acid, ethyl ester,
4-amino-6-chloro-2,9-dimethyl-9H-pyrido[2,3-b]indole-3-carboxylic acid, methyl ester,
4-amino-9-methyl-2-phenyl-9H-pyrido[2,3-b]indole-3-carboxylic acid, methyl ester,
4-n-butylamino-2,9-dimethyl-9H-pyrido[2,3-b]indole-3-carboxylic acid, methyl ester,
2,9-dimethyl-4-methylamino-9-H-pyrido[2,3-b]indole-3-carboxylic acid, methyl ester,
2,9-dimethyl-4-dimethylamino-9H-pyrido[2,3-b]indole-3-carboxylic acid, methyl ester,
4-amino-2-methyl-9H-pyrido[2,3-b]indole-3-carboxylic acid, 2-propenyl ester,
4-amino-2,9-dimethyl-9H-pyrido[2,3-b]indole-3-carboxylic acid, 2-propenyl ester,
4-amino-9-ethyl-2-methyl-9H-pyrido[2,3-b]indole-3-carboxylic acid, methyl ester,
4-amino-2-methyl-9-(2-propenyl)-9H-pyrido[2,3-b]indole-3-carboxylic acid, methyl ester,
4-amino-2,9-dimethyl-9H-pyrido[2,3-b]indole-3-carboxylic acid, 2-propynyl ester,
4-amino-2-methyl-9H-pyrido[2,3-b]indole-3-carboxylic acid, n-propyl ester,
4-amino-2-methyl-9-n-pentyl-9H-pyrido[2,3-b]indole-3-carboxylic acid, methyl ester,
4-amino-2-methyl-9-(2-propynyl)-9H-pyrido[2,3-b]indole-3-carboxylic acid, methyl ester,
4-diacetylamino-2,9-dimethyl-9H-pyrido[2,3-b]indole-3-carboxylic acid, methyl ester,
4-acetylamino-2,9-dimethyl-9H-pyrido[2,3-b]indole-3-carboxylic acid, methyl ester,
4-amino-7-chloro-2,9-dimethyl-9H-pyrido[2,3-b]indole-3-carboxylic acid, methyl ester,
4-amino-7-chloro-2-methyl-9H-pyrido[2,3-b]indole-3-carboxylic acid, methyl ester,
4-amino-6-chloro-2-methyl-9H-pyrido[2,3-b]indole-3-carboxylic acid, methyl ester,
4-amino-2-phenyl-9-(2-propenyl)-9H-pyrido[2,3-b]indole-3-carboxylic acid, methyl ester,
4-amino-2,9-dimethyl-9H-pyrido[2,3-b]indole-3-carboxylic acid, n-propyl ester or
4-amino-2,9-dimethyl-6-hydroxy-9H-pyrido[2,3-b]indole-3-carboxylic acid, methyl ester.

9. 4-Amino-2,9-dimethyl-9H-pyrido[2,3-b]indole-3-carboxylic acid, cyclopropylmethyl ester,
4-amino-2-methyl-9-(2-propenyl)-9H-pyrido[2,3-b]indole-3-carboxylic acid, 2-propenyl ester,
2,9-dimethyl-4-ethylamino-9H-pyrido[2,3-b]indole-3-carboxylic acid, methyl ester, 4-amino-9-ethyl-2-methyl-9H-pyrido[2,3-b]indole-3-carboxylic acid, ethyl ester,
4-amino-9-cyclopropylmethyl-2-methyl-9H-pyrido[2,3-b]indole-3-carboxylic acid, methyl ester,
4-amino-9-cyclopropylmethyl-2-methyl-9H-pyrido[2,3-b]indole-3-carboxylic acid, ethyl ester,
2,9-dimethyl-4-methylamino-9H-pyrido[2,3-b]indole-3-carboxylic acid, ethyl ester, (Z)-2-butenedioate, or
4-amino-2-ethyl-9-methyl-9H-pyrido[2,3-b]indole-3-carboxylic acid, methyl ester.

10. 4-Amino-2,9-dimethyl-9H-pyrido[2,3-b]indole-3-carboxylic acid, ethyl ester.

11. A pharmaceutical composition for the treatment or prophylaxis of anxiety or depression, comprising an effective amount of a compound according to claim 1 and a pharmaceutically acceptable carrier.

12. A method of treatment or prophylaxis of anxiety or depression which comprises administering to the sufferer an effective amount of a compound according to claim 1.

13. A compound of formula (VI) or a salt, ester or amide thereof:

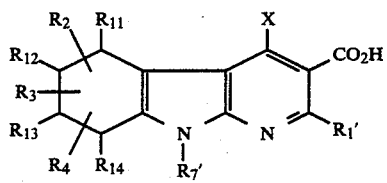

wherein $R_1'$ is $R_1$ as defined in claim 1 or a group convertible thereto, X is $NH_2$, OH or chloro, $R_2$, $R_3$ and $R_4$ are as defined in claim 1, and $R_{11}$, $R_{12}$, $R_{13}$ and $R_{14}$ are each hydrogen or $R_{11}$ and $R_{12}$, and $R_{13}$ and $R_{14}$ together represent a bond, and $R_7'$ represents $R_7$ as defined in claim 1 or an N-protecting group, provided that when X is $NH_2$, $R_{11}$, $R_{12}$, $R_{13}$ and $R_{14}$ represent two bonds, $R_1'$ is $R_1$ and $R_7'$ is $R_7$, the compound is the acid, an amide or benzyl ester in which the phenyl ring is optionally substituted by one or two of halogen, $CF_3$, $C_{1-6}$ alkoxy, $C_{1-6}$ alkyl or nitro, and provided that when X is $NH_2$, $R_2$, $R_3$, $R_4$, $R_{11}$, $R_{12}$, $R_{13}$ and $R_{14}$ are all hydrogen, $R_1'$ is methyl and $R_7'$ is benzyl or cyclohexyl, the compound is other than the ethyl ester.

14. 4-Amino-2-methyl-9-phenylmethyl-9H-pyrido[2,3-b]indole-3-carboxylic acid, ethyl ester,
4-amino-2-methyl-9H-pyrido[2,3-b]indole-3-carboxylic acid,
4-amino-9-(4-methoxyphenyl)methyl-2-methyl-5,6,7,8-tetrahydro-9H-pyrido[2,3-b]indole-3-carboxylic acid, methyl ester,
4-amino-9-(4-methoxyphenyl)methyl-2-methyl-9H-pyrido[2,3-b]indole-3-carboxylic acid, methyl ester,
4-amino-9-(4-methoxyphenyl)methyl-2-methyl-5,6,7,8-tetrahydro-9H-pyrido[2,3-b]indole-3-carboxylic acid, ethyl ester,
4-amino-9-(4-methoxyphenyl)methyl-2-methyl-9H-pyrido[2,3-b]indole-3-carboxylic acid, ethyl ester,
4-amino-9-(4-methoxyphenyl)methyl-2-methyl-9H-pyrido[2,3-b]indole-3-carboxylic acid,
4-amino-2,9-dimethyl-9H-pyrido[2,3-b]indole-3-carboxylic acid,
4-amino-9-(4-methoxyphenyl)methyl-2-phenyl-5,6,7,8-tetrahydro-9H-pyrido[2,3-b]indole-3-carboxylic acid, methyl ester,
4-amino-9-(4-methoxyphenyl)methyl-2-methyl-9H-pyrido[2,3-b]indole-3-carboxylic acid, 2-propenyl ester,
2,9-dimethyl-4-hydroxy-9H-pyrido[2,3-b]indole-3-carboxylic acid, methyl ester,
4-chloro-2,9-dimethyl-9H-pyrido[2,3-b]indole-3-carboxylic acid, methyl ester or
4-amino-2-methyl-9H-pyrido[2,3-b]indole-3-carboxamide.

* * * * *